United States Patent
Pentelute et al.

(10) Patent No.: US 9,731,029 B2
(45) Date of Patent: Aug. 15, 2017

(54) PROTEIN RETROSPLICING ENABLED BY A DOUBLE LIGATION REACTION

(71) Applicant: Massachusetts Institute of Technology, Cambridge, MA (US)

(72) Inventors: Bradley L. Pentelute, Cambridge, MA (US); Xiaoli Liao, Cambridge, MA (US); Amy E. Rabideau, Cambridge, MA (US); Jingjing Ling, Cambridge, MA (US); Rocco L. Policarpo, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 447 days.

(21) Appl. No.: 14/402,915

(22) PCT Filed: May 21, 2013

(86) PCT No.: PCT/US2013/042107
§ 371 (c)(1),
(2) Date: Nov. 21, 2014

(87) PCT Pub. No.: WO2013/177221
PCT Pub. Date: Nov. 28, 2013

(65) Prior Publication Data
US 2015/0152134 A1 Jun. 4, 2015

Related U.S. Application Data

(60) Provisional application No. 61/649,866, filed on May 21, 2012, provisional application No. 61/649,421, filed on May 21, 2012.

(51) Int. Cl.
| | |
|---|---|
| C07K 1/107 | (2006.01) |
| A61K 47/48 | (2006.01) |
| C07K 1/04 | (2006.01) |
| C07K 2/00 | (2006.01) |
| C12P 21/06 | (2006.01) |
| A61K 31/7056 | (2006.01) |
| A61K 39/395 | (2006.01) |

(52) U.S. Cl.
CPC .... *A61K 47/48346* (2013.01); *A61K 31/7056* (2013.01); *A61K 39/395* (2013.01); *A61K 47/48246* (2013.01); *A61K 47/48261* (2013.01); *C07K 1/047* (2013.01); *C07K 1/107* (2013.01); *C07K 2/00* (2013.01); *C12P 21/06* (2013.01)

(58) Field of Classification Search
None
See application file for complete search history.

(56) References Cited

U.S. PATENT DOCUMENTS

| | | |
|---|---|---|
| 5,770,380 A | 6/1998 | Hamilton et al. |
| 2002/0169282 A1 | 11/2002 | Canne et al. |
| 2007/0082378 A1 | 4/2007 | Kent et al. |

FOREIGN PATENT DOCUMENTS

| | | |
|---|---|---|
| WO | WO 2005/051976 A2 | 6/2005 |
| WO | WO 2012/096926 A2 | 7/2012 |
| WO | WO 2012/142659 A1 | 10/2012 |

OTHER PUBLICATIONS

[No Author Listed] A Brief Introduction to Morpholino Antisense. Gene Tools, last accessed May 16, 2013, 2 pages. http://www.gene-tools.com/node/13.
[No Author Listed] Morpholino. Wikipedia, last accessed May 16, 2013, 10 pages. http://en.wikipedia.org/wiki/Morpholino.
[No Author Listed] Welcome to MOrpholino DataBase! MODB Morpholino Database, last accessed May 16, 2013, 2 pages. http://www.morpholinodatabase.org/.
Bang et al., Kinetically controlled ligation for the convergent chemical synthesis of proteins. Angew Chem Int Ed Engl. Jun. 12, 2006;45(24):3985-8.
Bavikar et al., Chemical synthesis of ubiquitinated peptides with varying lengths and types of ubiquitin chains to explore the activity of deubiquitinases. Angew Chem Int Ed Engl. Jan. 16, 2012;51(3):758-63. doi: 10.1002/anie.201106430. Epub Nov. 30, 2011.
Bowen et al., Twenty years since 'antibody mimics' by molecular imprinting were first proposed: A critical perspective. Molecular Imprinting. 2012;35-40.
Chatterjee et al., Disulfide-directed histone ubiquitylation reveals plasticity in hDot1L activation. Nat Chem Biol. Apr. 2010;6(4):267-9. doi: 10.1038/nchembio.315. Epub Mar. 7, 2010.
Chen et al., A general strategy for the evolution of bond-forming enzymes using yeast display. Proc Natl Acad Sci U S A. Jul. 12, 2011;108(28):11399-404. doi: 10.1073/pnas.1101046108. Epub Jun. 22, 2011.
Clancy et al., Sortase transpeptidases: insights into mechanism, substrate specificity, and inhibition. Biopolymers. 2010;94(4):385-96. doi: 10.1002/bip.21472.
Collier et al., Diphtheria toxin subunit active in vitro. Science. Jun. 6, 1969;164(3884):1179-81.
Collier, Effect of diphtheria toxin on protein synthesis: inactivation of one of the transfer factors. J Mol Biol. Apr. 14, 1967;25(1):83-98.
Dawson et al., Synthesis of proteins by native chemical ligation. Science. Nov. 4, 1994;266(5186):776-9.
Evans et al., Semisynthesis of cytotoxic proteins using a modified protein splicing element. Protein Sci. Nov. 1998;7(11):2256-64.
Gebauer et al., Engineered Protein scaffolds as next-generation antibody therapeutics. ScienceDirect. 2009;13:245-55.
Guo et al., Sortase-catalyzed peptide-glycosylphosphatidylinositol analogue ligation. J Am Chem Soc. Jul. 29, 2009;131(29):9878-9. doi: 10.1021/ja903231v.

(Continued)

*Primary Examiner* — Christopher M Gross
(74) *Attorney, Agent, or Firm* — Wolf, Greenfield & Sacks, P.C.

(57) ABSTRACT

Proteins containing a C-terminal thioester are important intermediates in semi-synthesis. Currently there is one main method for the synthesis of protein thioesters that relies upon the use of engineered inteins. The invention involves, in some aspects a method, utilizing Sortase A, for preparation of recombinant proteins containing a C-terminal αthioester. This new method for double ligation is useful for synthesizing new or naturally occurring molecules such as a protein thioester.

16 Claims, 18 Drawing Sheets

(56) References Cited

OTHER PUBLICATIONS

Hackeng et al., Protein synthesis by native chemical ligation: expanded scope by using straightforward methodology. Proc Natl Acad Sci U S A. Aug. 31, 1999;96(18):10068-73.
Johnson et al., Insights into the mechanism and catalysis of the native chemical ligation reaction. J Am Chem Soc. May 24, 2006;128(20):6640-6.
Johnson et al., Towards the total chemical synthesis of integral membrane proteins: a general method for the synthesis of hydrophobic peptide-thioester building blocks. Tetrahedron Lett. Mar. 5, 2007;48(10):1795-1799.
Kent, Total chemical synthesis of proteins. Chem Soc Rev. Feb. 2009;38(2):338-51. doi: 10.1039/b700141j. Epub Sep. 16, 2008.
Kobashigawa et al., Attachment of an NMR-invisible solubility enhancement tag using a sortase-mediated protein ligation method. J Biomol NMR. Mar. 2009;43(3):145-50. doi: 10.1007/s10858-008-9296-5. Epub Jan. 13, 2009.
Mazmanian et al., Staphylococcus aureus sortase, an enzyme that anchors surface proteins to the cell wall. Science. Jul. 30, 1999;285(5428):760-3.
Milne et al., Protective antigen-binding domain of anthrax lethal factor mediates translocation of a heterologous protein fused to its amino- or carboxy-terminus. Mol Microbiol. Feb. 1995;15(4):661-6.
Möhlmann et al., In vitro sortagging of an antibody fab fragment: overcoming unproductive reactions of sortase with water and lysine side chains. Chembiochem. Jul. 25, 2011;12(11):1774-80. doi: 10.1002/cbic.201100002. Epub Jun. 7, 2011.
Muir et al., Expressed protein ligation: a general method for protein engineering. Proc Natl Acad Sci U S A. Jun. 9, 1998;95(12):6705-10.
Muir, Semisynthesis of proteins by expressed protein ligation. Annu Rev Biochem. 2003;72:249-89. Epub Feb. 27, 2003.
Murakami et al., Chemical Synthesis of an Erythropoietin Glycoform Containing a Complex-type Disialyloligosaccharide. Agnew. Chem. Int. Ed. Engl. 2012;51:3567-72.
Nagorny et al., Probing the frontiers of glycoprotein synthesis: the fully elaborated β-subunit of the human follicle-stimulating hormone. Angew Chem Int Ed Engl. Jan. 23, 2012;51(4):975-9. doi: 10.1002/anie.201107482. Epub Dec. 9, 2011.
Navarre et al., Proteolytic cleavage and cell wall anchoring at the LPXTG motif of surface proteins in gram-positive bacteria. Mol Microbiol. Oct. 1994;14(1):115-21.
Pentelute et al., Chemical dissection of protein translocation through the anthrax toxin pore. Angew Chem Int Ed Engl. Mar. 1, 2011;50(10):2294-6. doi: 10.1002/anie.201006460. Epub Feb. 3, 2011.
Piotukh et al., Directed evolution of sortase A mutants with altered substrate selectivity profiles. J Am Chem Soc. Nov. 9, 2011;133(44):17536-9. doi: 10.1021/ja205630g. Epub Oct. 13, 2011.
Popp et al., Making and breaking peptide bonds: protein engineering using sortase. Angew Chem Int Ed Engl. May 23, 2011;50(22):5024-32. doi: 10.1002/anie.201008267. Epub Apr. 27, 2011.
Popp et al., Sortagging: a versatile method for protein labeling. Nat Chem Biol. Nov. 2007;3(11):707-8. Epub Sep. 23, 2007.
Proft, Sortase-mediated protein ligation: an emerging biotechnology tool for protein modification and immobilisation. Biotechnol Lett. Jan. 2010;32(1):1-10. doi: 10.1007/s10529-009-0116-0. Epub Sep. 1, 2009.
Samantaray et al., Peptide-sugar ligation catalyzed by transpeptidase sortase: a facile approach to neoglycoconjugate synthesis. J Am Chem Soc. Feb. 20, 2008;130(7):2132-3. doi: 10.1021/ja077358g. Epub Jan. 30, 2008.
Scheuermann et al., Histone H2A deubiquitinase activity of the Polycomb repressive complex PR-DUB. Nature. May 13, 2010;465(7295):243-7. doi: 10.1038/nature08966. Epub May 2, 2010.
Schnölzer et al., In situ neutralization in Boc-chemistry solid phase peptide synthesis. Rapid, high yield assembly of difficult sequences. Int J Pept Protein Res. Sep.-Oct. 1992;40(3-4):180-93.
Severinov et al., Expressed protein ligation, a novel method for studying protein-protein interactions in transcription. J Biol Chem. Jun. 26, 1998;273(26):16205-9.
Ton-That et al., Anchoring of surface proteins to the cell wall of Staphylococcus aureus. Sortase catalyzed in vitro transpeptidation reaction using LPXTG peptide and NH(2)-Gly(3) substrates. J Biol Chem. Mar. 31, 2000;275(13):9876-81.
Tsukiji et al., Sortase-mediated ligation: a gift from Gram-positive bacteria to protein engineering. Chembiochem. Mar. 23, 2009;10(5):787-98. doi: 10.1002/cbic.200800724.
Vila-Perelló et al., Biological applications of protein splicing. Cell. Oct. 15, 2010;143(2):191-200. doi: 10.1016/j.cell.2010.09.031.
Wood et al., Optimized conjugation of a fluorescent label to proteins via intein-mediated activation and ligation. Bioconjug Chem. Mar.-Apr. 2004;15(2):366-72.
Wu et al., Sortase A-catalyzed peptide cyclization for the synthesis of macrocyclic peptides and glycopeptides. Chem Commun (Camb). Aug. 28, 2011;47(32):9218-20. doi: 10.1039/c1cc13322e. Epub Jul. 8, 2011.
Wu et al., Sortase A-catalyzed transpeptidation of glycosylphosphatidylinositol derivatives for chemoenzymatic synthesis of GPI-anchored proteins. J Am Chem Soc. Feb. 10, 2010;132(5):1567-71. doi: 10.1021/ja906611x.
Xu et al., Intein-mediated ligation and cyclization of expressed proteins. Methods. Jul. 2001;24(3):257-77.
Yamamoto et al., Expansion of the sortase-mediated labeling method for site-specific N-terminal labeling of cell surface proteins on living cells. Chem Commun (Camb). Mar. 7, 2009;(9):1022-4. doi: 10.1039/b818792d. Epub Jan. 7, 2009.
Young et al., Anthrax toxin: receptor binding, internalization, pore formation, and translocation. Annu Rev Biochem. 2007;76:243-65.
Mao et al., Sortase-mediated protein ligation: a new method for protein engineering. J Am Chem Soc. 2004;126(9):2670-1.
Ling et al., Protein thioester synthesis enabled by sortase. J Am Chem Soc. Jul. 4, 2012;134(26):10749-52. doi:10.1021/ja302354v. Epub Jun. 19, 2012.

LF$_N$-COSR

LF$_N$-DTA-COSR eGFP-COSR eGFP-COSR

LF$_N$-COSR

LF$_N$-DTA-COSR

LF$_N$-L-linker-COSR and Cys-DTA t=0 hr

LF$_N$-L-linker-COSR and Cys-DTA t=5 hr

LF$_N$-L-linker-DTA eGFP reaction with 50 µM $G_5LRL$ eGFP reaction with 500 µM $G_5LRL$ Time [min]

SrtA reaction 30 minutes

NCL reaction 1 hour

Purified AF-$G_5$-G

SrtA reaction 30 minutes
9304.0
8663.1

NCL reaction 1 hour
11109.8

Purified AF-$G_5$-G

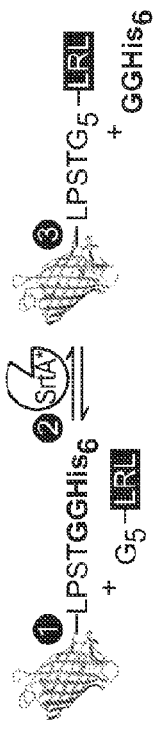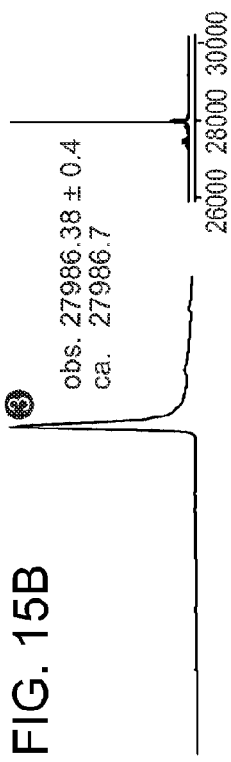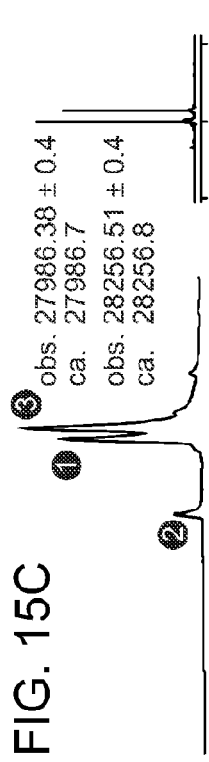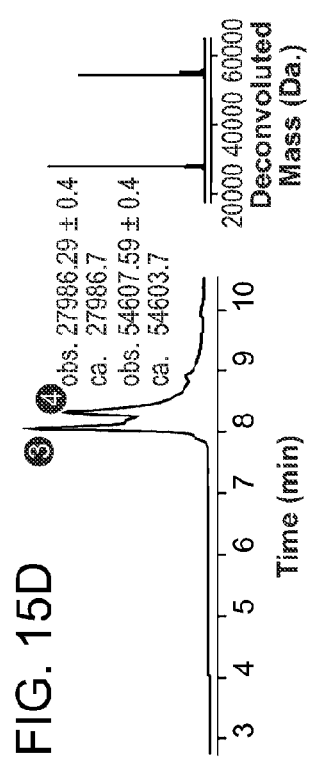
FIG. 15A
FIG. 15B
FIG. 15C
FIG. 15D
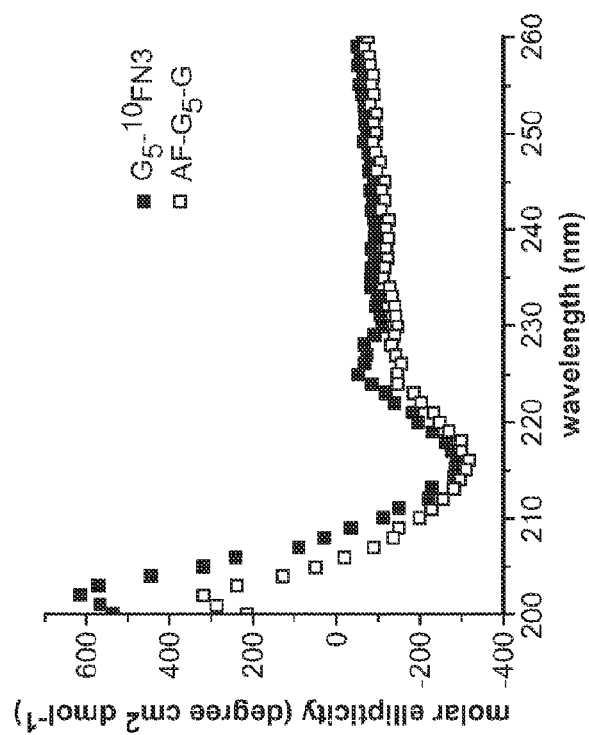
FIG. 14

Time (min)

Deconvoluted Mass. (Da.)

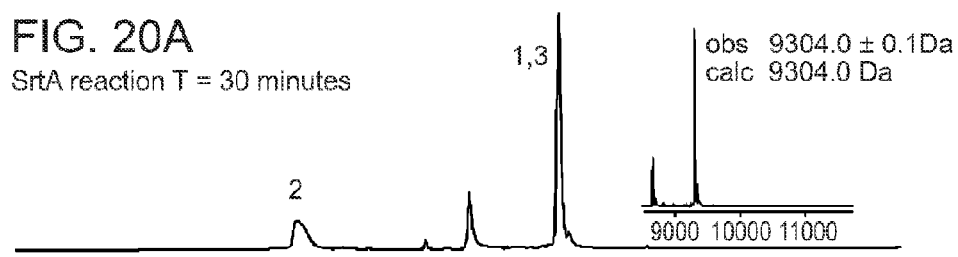
FIG. 20A SrtA reaction T = 30 minutes
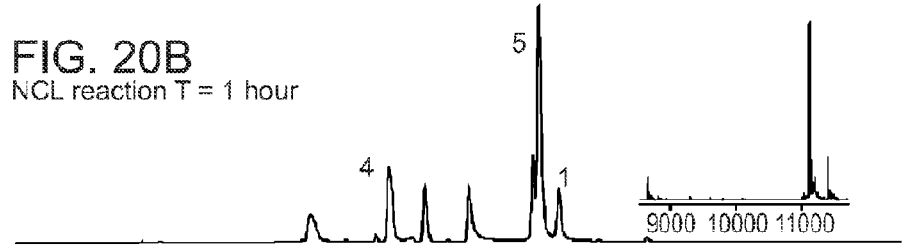
FIG. 20B NCL reaction T = 1 hour
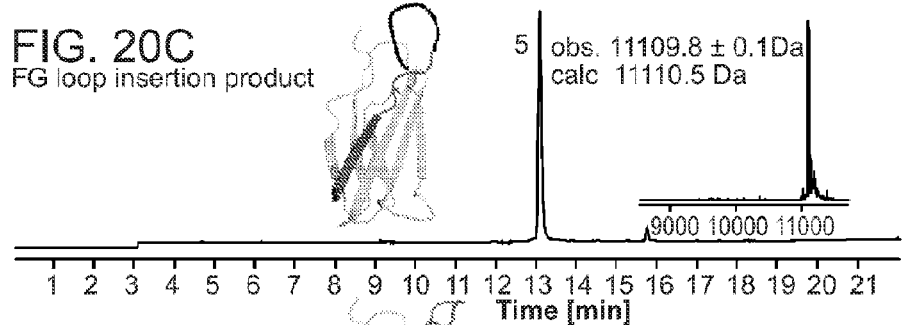
FIG. 20C FG loop insertion product
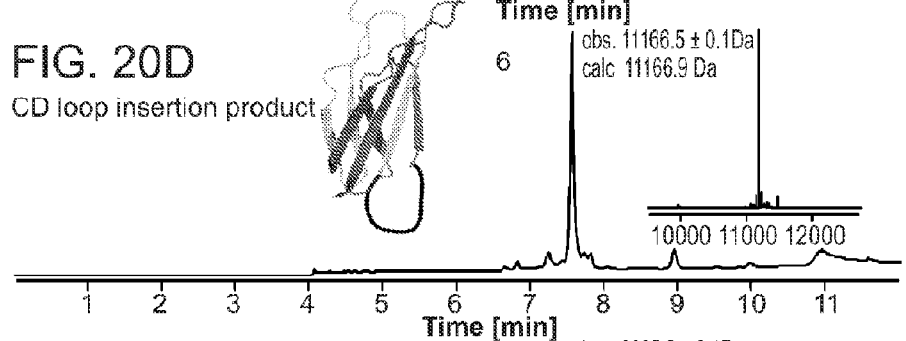
FIG. 20D CD loop insertion product
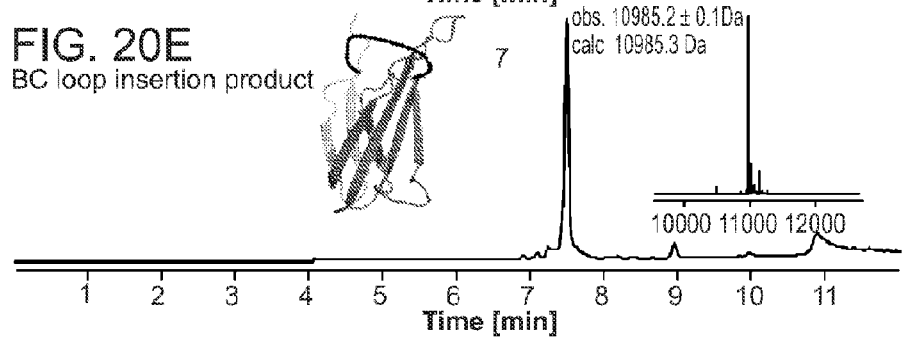
FIG. 20E BC loop insertion product Protein αthioester synthesis using SrtA

PROTEIN RETROSPLICING ENABLED BY A DOUBLE LIGATION REACTION

RELATED APPLICATIONS

This application is a national stage filing under U.S.C. §371 of PCT International Application PCT/US2013/042107, filed May 21, 2013, which claims priority under 35 U.S.C. §119(e) to U.S. Provisional Application Ser. No. 61/649,866 entitled "PROTEIN RETROSPLICING ENABLED BY A DOUBLE LIGATION REACTION," filed on May 21, 2014 and to U.S. Provisional Application Ser. No. 61/649,421, entitled "TRANSLOCATION OF NON-NATURAL CHEMICAL ENTITIES THROUGH ANTHRAX PROTECTIVE ANTIGEN PORE," filed on May 21, 2012, which are herein incorporated by reference in their entirety.

BACKGROUND OF INVENTION

Chemical tailoring of proteins is a powerful approach to investigate structure function relationships and the role of post-translational modifications.[1-6] Protein semi-synthesis[4,7] and total synthesis[8] are commonly used to introduce novel functionalities into proteins. Both approaches rely on native chemical ligation (NCL)—a chemoselective amide forming reaction between an $\alpha$thioester and an N-terminal cysteine moiety.[9] When protein $\alpha$thioesters are generated from engineered inteins and then modified with NCL the process is referred to as expressed protein ligation.[10-12] Inteins are protein self-splicing elements that can be engineered to generate protein $\alpha$thioesters after self-cleavage in the presence of small molecule thiol.[10-12] Despite a number of new methods for the chemical synthesis of peptide $\alpha$thioesters, intein mediated synthesis of protein $\alpha$thioesters is the only route to generate this important functionality needed for semi-synthesis.

SUMMARY OF INVENTION

The invention in some aspects relates to a method for preparing proteins having non-natural entities incorporated therein. The method is a double ligation reaction that, for instance, allows chemoselective insertion of synthetic peptides/proteins, nucleic acids, peptidomimetics and other molecules such as labels into folded proteins.

The invention in some aspects is a method of performing a continuous flow enzymatic ligation reaction by flowing a N-terminal protein and a peptide thioester over a stationary phase containing a cysteine transpeptidase enzyme, wherein a N-terminal protein-COSR product is formed, and flowing a C-terminal protein over the stationary phase, wherein the C-terminal protein domain has a cysteine at the N-termini, to produce a modified protein having a chemical entity linking the N-terminal protein domain and the C-terminal protein domain.

In other aspects the invention is a method for performing an enzymatic double ligation reaction by performing a continuous flow sortagging reaction on a substrate and nucleophile wherein the nucleophile is present in a low micromolar concentration, in the presence of an enzyme, wherein the enzyme catalyzes a high efficiency double ligation reaction. In some embodiments the nucleophile is a peptide thioester. In other embodiments the enzyme is attached to a stationary phase. Optionally, the enzyme is a cysteine transpeptidase. In other embodiments the substrate is a N-terminal protein.

In some embodiments the low micromolar concentration of nucleophile is less than 300 micromolar. In other embodiments it is 5-290 micromolar, 10-200 micromolar, 10-100 micromolar, 10-50 micromolar, 10-20 micromolar, or 20-40 micromolar.

In some aspects the invention is a method involving performing a ligation reaction of a N-terminal protein domain with a peptide thioester in the presence of a cysteine transpeptidase enzyme, such as SrtA enzyme, to produce a N-terminal protein domain-COSR product, and reacting the N-terminal protein domain-COSR product with a C-terminal protein domain, wherein the C-terminal protein domain has a cysteine at the N-termini, to produce a modified protein having a chemical entity linking the N-terminal protein domain and the C-terminal protein domain. In other aspects the methods are performed as described wherein one or more of the N-terminal or C-terminal protein domains is a whole protein.

SrtA enzyme is the sortase A enzyme. In some embodiments SrtA enzyme is the native naturally occurring SrtA. In other embodiments SrtA is a SrtA variant, such as SrtA*. The ligation reaction may be performed in a sortase buffer.

In some embodiments, the N-terminal protein domain is recombinantly expressed as a SUMO-protein having a SUMO tag, prior to the ligation reaction. The SUMO tag may be removed using SUMO protease.

In some embodiments the peptide thioester is $G_n$-Xaa-COSR (SEQ ID NOs:1-3), wherein n is 1-6 and wherein Xaa is any amino acid. In other embodiments the peptide thioester is $G_n$-Xaa-COSR (SEQ ID NOs:4-5), wherein n is 3-5 and, wherein Xaa is Gly, Phe, Ser or Leu. In yet other embodiments the peptide thioester is GGGGG-Xaa-COSR (SEQ ID NOs:5), wherein Xaa is Gly, Phe, Ser or Leu. In some embodiments the peptide thioester is $G_n$-$X_m$-COSR (SEQ ID NOs:6-23), wherein n is 1-6, m is 1-6, and wherein X is an amino acid, naturally occurring or non-naturally occurring. X may be a D-amino acid (SEQ ID NOs:24-42). In yet other embodiments the peptide thioester is $G_n$-Y-COSR (SEQ ID NOs:43-45), wherein n is 1-6 and wherein Y is a non-amino acid chemical entity. Y may be a PEG unit (SEQ ID NOs:46-48).

The method may be performed without an engineered intein in some embodiments.

The C-terminal protein domain and the N-terminal protein domain, in some embodiments are protein domains of the same protein. Alternatively, the C-terminal protein domain and the N-terminal protein domain are protein domains of different proteins.

In yet other embodiments the C-terminal protein domain and the N-terminal protein domain are recombinantly produced.

A modified protein domain is provided in other aspects. The modified protein domain is an N-terminal domain of a protein linked to a thioester, wherein the N-terminal domain of the protein is a single domain of a multi-domain protein, and wherein the N-terminal domain is linked to the thioester in the flexible hinge region that separates the N-terminal domain from a C-terminal domain of the protein.

In some aspects the invention is a method of producing a polypeptide library comprising a) covalently binding a set of N-terminal protein domains to a solid support via a linker, wherein the linker comprises a cleavable moiety stable under ligating conditions and the N-terminal protein domains are each bound to the linker at its N-terminus; b) introducing a set of peptide thioesters in the presence of a SrtA enzyme to produce a set of N-terminal protein domain-COSR products; and c) introducing a set of C-terminal protein domains, having a cysteine at the N-termini, to produce a set of modified proteins having unique chemical entities linking the N-terminal protein domains and the C-terminal protein domains, wherein the set of modified proteins forms the polypeptide library.

In other aspects the invention is a modified protein, having a first protein domain linked to a second protein domain through a D-peptide fragment, wherein the first and second protein domains are recombinantly expressed protein domains. In some embodiments the D-peptide fragment is a peptide having a single D amino acid.

A combinatorial library is also an aspect of the invention. The combinatorial library has a plurality of modified proteins, each protein comprising a first domain linked to a second protein domain through a flexible linker, wherein each protein in the plurality of modified proteins has a unique linker. In some embodiments the proteins are antibodies, such as modified forms of Avastin.

According to other aspects of the invention a kit having one or more containers housing a synthetic peptide thioester, a SrtA enzyme, and instructions for performing a double ligation reaction is provided. In some embodiments the synthetic peptide thioester has a Gn sequence, wherein n is 1-10. In other embodiments the synthetic peptide thioester has an amine or a hydrazine.

A system having a microreactor having tubing attached through an outlet to a vacuum manifold, wherein the vacuum manifold is positioned to apply a vacuum through a microreactor body, wherein the microreactor body has an inlet for accepting a delivery of compounds is provided according to other aspects of the invention.

In yet other aspects the invention is a method involving positioning a stationary phase containing a cysteine transpeptidase enzyme within the microreactor body of claim 36, adding a mixture of a N-terminal protein and a peptide thioester in a sortase buffer to the microreactor under flow conditions, and flowing a C-terminal protein over the stationary phase, wherein the C-terminal protein domain has a cysteine at the N-termini, to produce a modified protein having a chemical entity linking the N-terminal protein domain and the C-terminal protein domain.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF DRAWINGS

The figures are illustrative only and are not required for enablement of the invention disclosed herein.

FIG. 14. Circular Dichroism spectra of $G_{5-10}FN_3$ (SEQ ID NO:106 and AF-$G_5$-G (SEQ ID NO:105).

FIG. 15 is a set of graphs depicting that flow based sortagging can be performed at low nucleophile concentrations. A model flow-based platform was designed that employed a protein substrate eGFP-LPSTGG-His6 (SEQ ID NO:80), glycine nucleophile GGGG-LRL-CONH2 (SEQ ID NO:107), and SrtA*-His6 (FIG. 15A). A reaction was performed in a microreactor using eGFP-LPSTGG-His6 and G5LRL in sortase buffer (FIG. 15B). LCMS analysis revealed that batch sortagging reactions provided minimal desired product (FIG. 15C). Ni-NTA treatment successfully removed unreacted starting material but major dimer formation was observed (FIG. 15D).

FIG. 20. LCMS characterization of the double ligation reactions and products. (a-c) Total ion current (TIC) traces and deconvoluted mass of peaks extracted from 12-15 minutes on TIC traces of A-F and G complementation reaction. 120 μM A-F_LPSTGG (SEQ ID NO:59) fragment reacts with 240 μM $G_5COSR$ (SEQ ID NO:60) in the presence of 5 μM SrtA for 30 minutes at pH 7.5 (a), then 240 μM fragment G is added and react for 1 hour at pH 7.0 (b). d). LCMS data of $_{10}FN_3$ product with G5 inserted at the CD loop. e). LCMS data of $_{10}FN_3$ product with G5 inserted at the BC loop.

DETAILED DESCRIPTION

Figure 1A:
FIG. 1. LC data for peptide $^\alpha$thioester synthesis using SrtA* followed by NCL. (a) SrtA*-mediated ligation (SML) of model peptide. (b) Analytical RP-HPLC of crude SML reaction for t=0 min and t=30 min. Reaction conditions: 1 mM G$_5$F-COSR (SEQ ID NO:49), 500 µM KLPETGG (SEQ ID NO:50), 5 µM SrtA*, SrtA* buffer, pH 7.5. (c) Native chemical ligation (NCL) with sortagged thioester reaction product. (d) Analytical RP-HPLC of purified NCL reaction product. Reaction conditions are reported in the supporting information. All analytical RP-HPLC signals are measured at 214 nm. Δ: impurity peak.
Figure 1B:
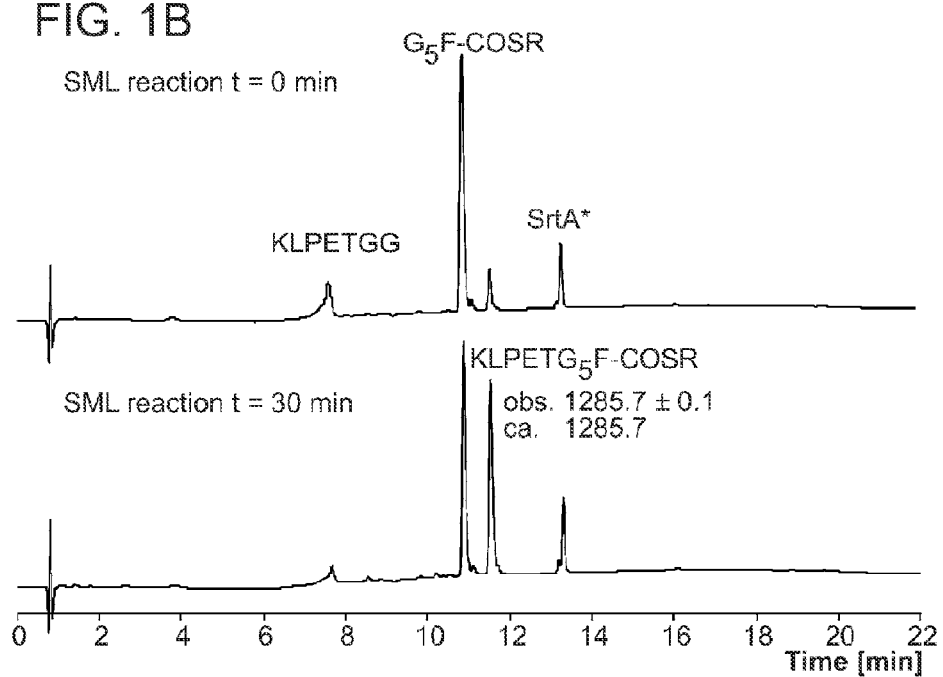
Figure 1C:
Figure 1D:
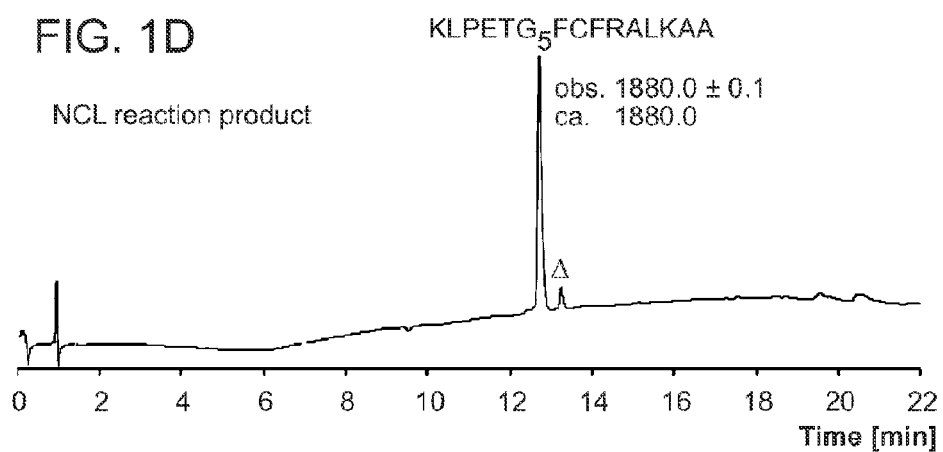

The invention in some aspects relates to a novel double ligation reaction that allows for the chemoselective insertion of non-natural entities such as peptides/proteins, nucleic acids, peptidomimetics and other molecules such as labels into folded proteins. The reaction involves the breakage of one amide bond and the formation of two others. The reaction can occur in minutes at room temperature in aqueous buffer, providing a rapid, powerful approach that allows for the at will insertion of non-natural or naturally occurring chemical entities into folded proteins, a method which was not previously possible.

A non-natural species or entity, as used herein refers to a compound that is not ordinarily found in a specific position within the protein of interest. Non-natural entities, may therefore include naturally occurring amino acids, as long as it is not the amino acid normally found at that specific position within a protein. A non-natural species or entity is also referred to in the claims as Xaa or Xm and includes but is not limited to naturally occurring amino acids, non-naturally occurring amino acids, such as D-form amino acids, labeled probes, peptidomimetics, and PEG units. The insertion of the entity will depend on the installation of the appropriate reaction partners. In certain embodiments, the non-natural species or entity is one or more heme groups, rhodopsin molecules, vitamins, biotins, fatty acids, lipids, carbohydrates, polymers, or inorganic elements, ions, or clusters.

A number of applications of the methods and related products described herein are envisioned. For example, chemical probes can be introduced into proteins for structure function studies. Additionally, combinatorial libraries of proteins can be prepared that contain any of the thousands of non-natural amino acids including the D-form that can then be used to discover novel protein therapeutics. Additionally, therapeutic antibodies, such as Avastin, can be significantly tailored to favor a particular therapeutic profile and increase the potency.

The basic method of the invention involves a double ligation reaction that links together an N-terminal protein domain and a C-terminal protein domain with the insertion of one or more non-natural species or entities between the two domains, preferably in a linker.

A protein domain (N-terminal or C-terminal), as used herein, refers to a region of a protein, that is less than the whole protein. The domain may, in some instances, be a region of the protein connected to one or more other protein regions through a linker. The protein domain, may be an antibody or an antibody fragment or domain thereof. The length of the protein domain may be at least or at most 15, 16, 17, 18, 19, 20, 21, 22, 23, 24, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 350, 400, 450, 500, 550, 600, 650, 700, 750, or 800 amino acid residues in length, or any range derivable therein. Longer lengths are possible.

The protein domains are preferably produced recombinantly. Recombinant technology is well known in the art, and the claimed invention is not limited by any specific methodology. During the recombinant synthesis an LPXTG tag (SEQ ID NO:61) may be added at the C-termini of the N-terminal protein domain. Additionally a cysteine may be added at the N-termini of the C-terminal protein domain.

The protein domains may be two domains of the same protein. In this embodiment the proteins may be split at a linker region that is linking the two domains. The linker region, may be, for instance a flexible linker region. Alternatively, the protein domains may be from different proteins and may be linked together to create an optimized or unique protein structure.

A linker may be a covalent linkage linking various moieties. For example, a linker may be a naturally occurring amino acid linker that connects two protein domains. Alternatively a linker may link a first peptide segment and a solid support, and such a linker may optionally comprises any number of moieties, including a cleavable handle, a cleavable linker, complementary functional groups capable of chemoselectively forming a covalent bond (e.g., amino-oxy and ketone to form an oxime).

A peptide or protein or polypeptide, as used herein, refers to a polymer of at least two monomers, wherein the monomers are amino acids, sometimes referred to as amino acid residues, which are joined together via an amide bond. For purposes of this invention, the terms "peptide," "polypeptide," and "protein," are largely interchangeable as all three types can be used in aspects of the methods described herein.

As used herein, the term amino refers to an amino acid having protected or unprotected side chains. Amino acids include the L and D isoforms of chiral amino acids. An amino acid sequence set forth herein, such as "LPXTG" (SEQ ID NO:61) orders the amino acid residues from the N-terminus to the C-terminus in a left-to-right manner, unless otherwise indicated from the context. As used herein, the term "side chain" refers to the substituent at the α-carbon atom of an amino acid.

The first ligation reaction involves the ligation of the N-terminal protein domain with a peptide thioester in the presence of a cysteine transpeptidase enzyme such as a SrtA enzyme to produce a N-terminal protein domain-COSR product. A "peptide thioester" as used herein refers to a peptide having a thioester group. A thioester is a moiety represented by -COSR. For example, a peptide thioester may be represented as "peptide-COSR", wherein the R group may be any number of groups. In preferred embodiments the peptide component includes 1-6 Gs in order to enhance the reaction.

The first ligation reaction is catalyzed by a cysteine transpeptidase enzyme such as a SrtA enzyme. A SrtA enzyme is a sortase. The term "sortase" refers to an enzyme that is a cysteine transpeptidase enzyme that can recognize a conserved carboxylic sorting motif and catalyze a transpeptidation reaction to anchor surface proteins to the cell wall envelope. The cysteine transpeptidase enzyme may be synthetic or naturally occurring. For instance it may be synthesized or obtained from a natural source such as a gram negative bacteria A preferred embodiment comprises the use of *Staphylococcus aureus* sortase A to catalyze a transpeptidation reaction between the N-terminal protein domain that is tagged with LPXTG (SEQ ID NO:61) at the C-terminus, and a second moiety containing the peptide thioester, typically in a sortase buffer. The term "SrtA" is used broadly to encompass naturally occurring SrtA as well as functional variants thereof. For instance, a preferred functional variant is SrtA*.

A second step of the method involves reacting the N-terminal protein domain-COSR product with a C-terminal protein domain to produce a modified protein having a chemical entity linking the N-terminal protein domain and the C-terminal protein domain. The chemical entity includes the non-natural species or entity, as discussed above, but may also include aspects of a protein such as a linker.

One advantage of the methods of the invention is that they can be performed without an engineered intein. The term "intein" refers to a protein that undergoes autoreaction resulting in the formation of novel peptide or amide linkages. Intein-mediated ligation is a well-established method to perform protein-protein conjugation (Xu and Evans Methods 24(3):257-277 (2001)) as well as protein-small molecule conjugation (Wood, et al., Bioconjug. Chem. 15(2):366-372 (2004)).

The modified proteins produced according to the methods described herein may be active or functional with respect to the native protein(s). For instance, the modified proteins may exhibit at least about or at most about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100%, or any range derivable therein of any activity or function of the native protein(s) based on a specific assay or measurement. Such conditions are well known to those of skill in the art.

The invention also contemplates methods for producing polypeptide libraries, as well as the libraries and component proteins therein. In some instances, the method involves covalently binding a set of N-terminal protein domains to a solid support via a linker, wherein the linker comprises a cleavable moiety stable under ligating conditions.

A cleavable linker is capable of being selectively cleaved under appropriate conditions. Such conditions vary depending on the use for the cleavable linker, but are well known to the skilled artisan. For instance, a cleavable linker should be stable under coupling and ligating conditions, deprotecting conditions (if needed), and washing conditions. Preferred cleavable linkers include photolabile linkers and TFA-labile linkers.

A solid support is a material having a surface and which is substantially insoluble when exposed to organic or aqueous solutions used for coupling, deprotecting, and cleavage reactions. Examples of solid phase materials include glass, polymers and resins, including polyacrylamide, PEG, polystyrene PEG-A, PEG-polystyrene, macroporous, POROS™, cellulose, reconstituted cellulose (e.g. Perloza), nitrocellulose, nylon membranes, controlled-pore glass beads, acrylamide gels, polystyrene, activated dextran, agarose, polyethylene, functionalized plastics, glass, silicon, aluminum, steel, iron, copper, nickel and gold. Such materials may be in the form of a plate, sheet, petri dish, beads, pellets, disks, or other convenient forms. Sheets of cellulose can be used as a solid phase in the present invention to accomplish spot ligation in a spatially addressable array. Many of the examples and embodiments described herein refer to resins, which are a type of solid phase, and one of ordinary skill in the art would understand that such examples are not meant to be limited to resins, but to solid phases in general. The terms solid phase and solid support are used herein interchangeably.

The methods result in the production of a plurality of modified proteins, each protein comprising a first domain linked to a second protein domain through a flexible linker, wherein each protein in the plurality of modified proteins has a unique linker. A unique linker, as used herein, refers to a linker having at least one non-natural species or entity.

Figure 22:
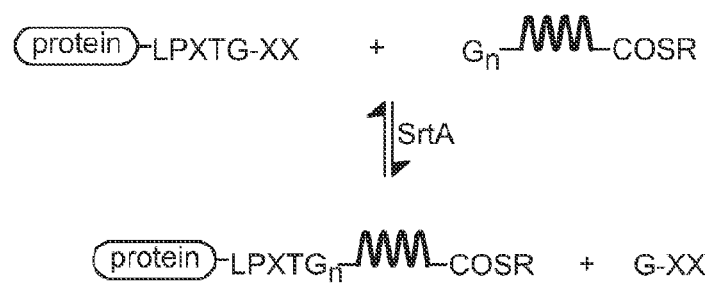
FIG. 22 is a schematic of the methods of the invention.

The experiments described herein are the first demonstration of a sortase-mediated approach for the facile synthesis of protein $^\alpha$thioesters (FIG. 22). We show that the calcium dependent enzyme sortase A (SrtA) from *Staphylococcus aureus* can be used to attach synthetic oligoglycine $^\alpha$thioesters to a number of different proteins with good yield and efficiency. In addition, this approach allowed us to prepare two different model cargo proteins and probe their translocation through anthrax toxin protective antigen. We found that the anthrax toxin pore can translocate cargo proteins into the cell that either contained an $^\alpha$thioester or a D-polypeptide segment linking two protein domains.

Sortases are a class of thiol-containing transpeptidases that anchor proteins to the bacterial cell wall.[13] SrtA recognizes a C-terminal LPXTG (SEQ ID NO:61) sequence and cleaves the threonine-glycine bond to form a thioacyl-linked intermediate.[14] This intermediate is primed to react with the N-terminal amino group of an oligoglycine motif. Recent effort has shown that sortases can be co-opted for the site-specific modification of proteins at the N or C-terminus.[15-25] This sortagging, transpeptidation reaction has been used extensively to attach virtually any water-soluble molecule to a protein of interest. Sortagging reactions are executed in calcium containing aqueous buffer (pH 7-8.5) at nanomolar to micromolar concentration of SrtA.[24] To carry out the sortagging reactions in water the N-terminal membrane spanning region of SrtA is removed.

The translocation of LF$_N$-DTA-COSR suggests that the amide bond can be replaced with a thioester without affecting passage through the pore. We plan to explore the possibility of using the thioester functionality to capture translocated proteins and their possible binding partners in the cytosol.

Our findings indicate that a model cargo protein containing non-natural modifications in the linker region is capable of translocation through the PA pore. Successful translocation of LF$_N$-D-linker-DTA demonstrates that the stereochemical constraints on PA-mediated translocation are minimal, provided that requirements for prepore binding and translocation initiation are met. This finding is in-line with a prior report investigating replacement of the N-terminus of LF$_N$ with a D-peptide segment.[35]

This method to generate an $^\alpha$thioester provides flexibility for covalent modification of proteins by interfacing key ligation approaches. The termini or linker regions of proteins can be site-specifically modified in a modular manner by the use of sortase-mediated ligation and native chemical ligation. Linker regions between two protein domains can be easily modified with natural or unnatural moieties by synthesizing various peptide thioesters. We demonstrated the utility of this approach by preparing a variant of LF$_N$-DTA in containing a D-peptide segment in the linker region. To the best of our knowledge, this is the first time that a D-peptide fragment has been installed between two recombinantly expressed protein domains.

Figure 12A:
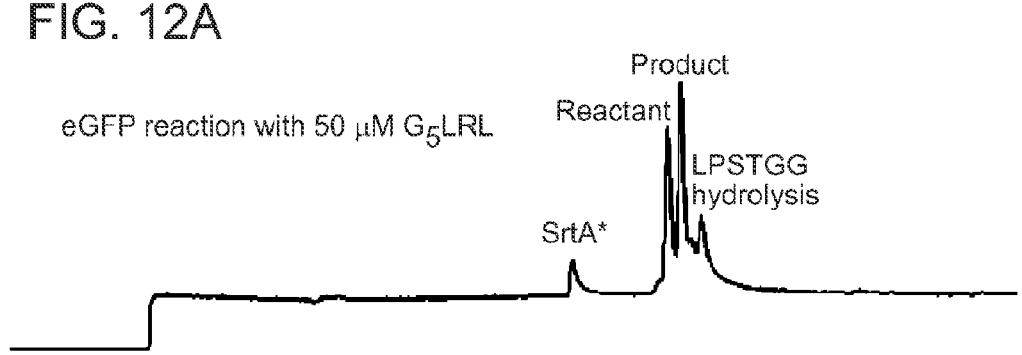
FIG. 12. LCMS data for hydrolysis analysis at varying $G_5$ nucleophile concentrations. (a) 50 μM $G_5LRL$. (b) 500 μM $G_5LRL$. Both 300 and 500 μM $G_5$ nucleophile showed minimal hydrolysis byproduct and proceeded with high yield. The traces above show total ion current chromatograms.
Figure 12B:
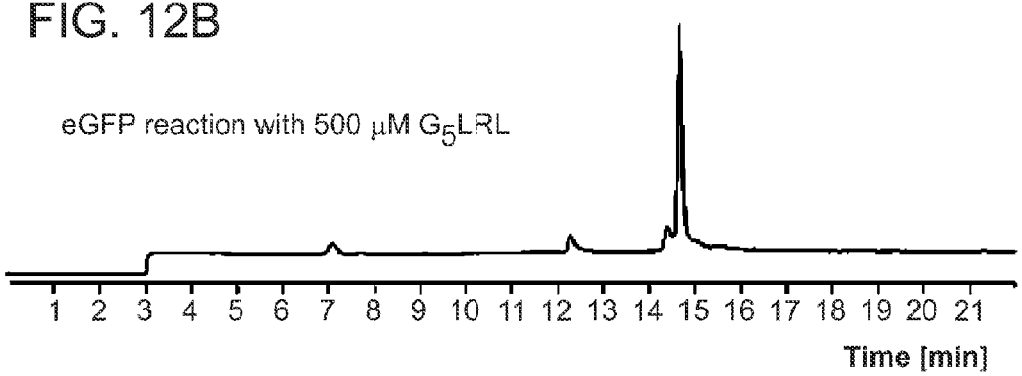
Figure 13A:
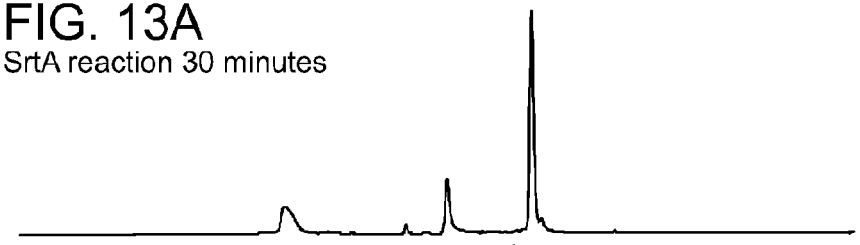
FIG. 13. LCMS characterization of the double ligation of AF and G fragments of $_{10}FN_3$. (a-c) total ion current (TIC) traces. (d-f) deconvoluted mass of peaks extracted from 12-15 minutes on TIC trace. 120 μM AF-LPSTGG (SEQ ID NO:59) fragment reacts with 240 μM $G_5COSR$ in the presence of 5 μM SrtA for 30 minutes at pH 7.5, then 240 μM fragment $^1C$-G is added and react for 1 hour at pH 7.0.
Figure 13B:
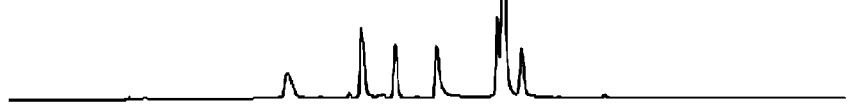
Figure 13C:
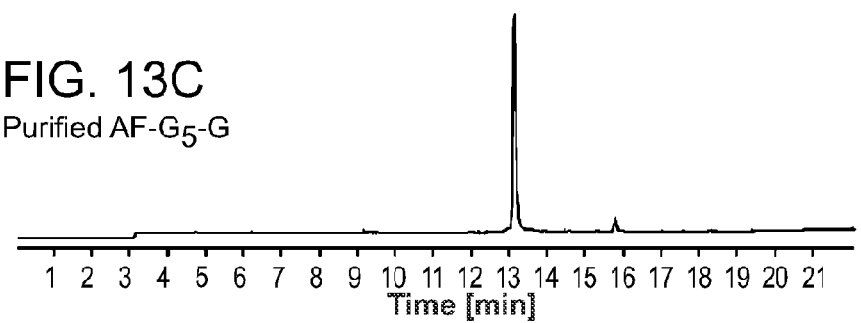
Figure 13D:
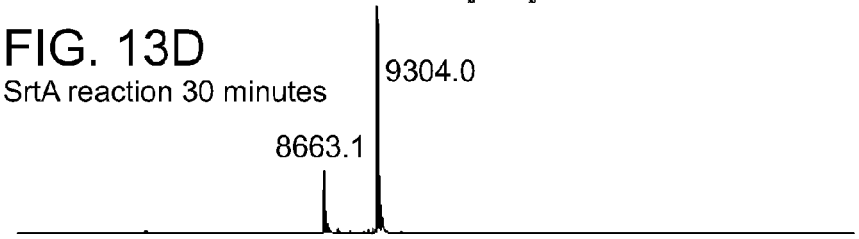
Figure 13E:
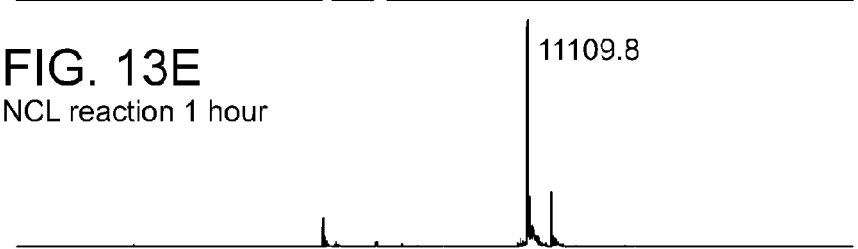
Figure 13F:
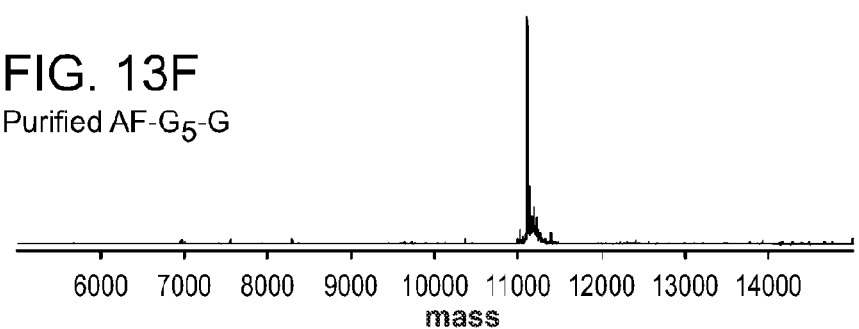

Our method of protein thioester generation could be used to overcome solubility limitations of sortagging reactions. We have found that sortagging efficiency directly parallels oligoglycine nucleophile concentration. Hydrolysis of LPXTG (SEQ ID NO:61) is a competing side-reaction for sortagging endeavors.[36,37] We found that optimal concentrations of oligogylcine needed to be 300 µM and above; at lower concentrations, we observed significant LPSTGG (SEQ ID NO:62) hydrolysis (FIG. 12). However, some oligoglycine peptides and proteins are insoluble at these concentrations. Our approach could be used to overcome this solubility limitation because short oligoglycine peptide thioesters tend to be highly soluble in aqueous solution. Moreover, if a given peptide thioester is still found to be insoluble it can be further modified to increase solubility by installing an Arg tag on the thioester leaving group.[38] After sortagging with a peptide $^\alpha$thioester, native chemical ligation can be carried out in solvents and buffers that denature sortase but solubilize the coupling partners. Common solubilizing agents that can be used in native chemical ligation reactions include denaturants (urea or guanidinium), detergents, and organic solvents.

However, it should be noted that the utility of sortagging is limited to ligations in which introduction of the LPXTG$_n$ (SEQ ID NO:61) moiety does not significantly alter protein structure. In cases when the LPXTG$_n$ (SEQ ID NO:61) segment may alter the properties of the protein, other ligation methods should be considered. Despite this limitation, sortagging has been used in numerous instances to modify proteins for biological study.[15-25] In our case, the LPXTG$_5$ (SEQ ID NO:63) linker did not affect the translocation of our LF$_N$-DTA constructs. One way to overcome this limitation would be to evolve sortase to recognize different and possibly shorter sequences. Recently, Piotukh et al. evolved SrtA to recognize FPXTG (SEQ ID NO: 64) or APXTG (SEQ ID NO:65) motif, suggesting this may be possible.[39]

In summary, we have developed a SrtA-mediated ligation approach for the synthesis of recombinant protein thioesters. Protein thioesters can be generated in 30 minutes with good yields, and pure products are isolated without elaborate purification steps.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1

Materials and Methods

Model Peptide Studies
Materials:
2-(1H-Benzotriazol-1-yl)-1,1,3,3-tetramethyluronium hexafluorophosphate (HBTU) and α-Boc protected L-amino acids (Chem-Impex International, IL and Peptide Institute, Japan). MBHA resin was obtained from Anaspec, CA.

N,N-Dimethylformamide (DMF), dichloromethane (DCM), diethyl ether, HPLC-grade acetonitrile, and guanidine hydrochloride were from VWR, PA. Trifluoroacetic acid (TFA) was purchased from NuGenTec, CA and Halocarbon, NJ. All other reagents were purchased from Sigma-Aldrich, MO and Invitrogen, CA, or as otherwise indicated.

Solid Phase Peptide Synthesis:

All model peptides were synthesized on a 0.2 mmol scale on 4-methylbenzhydrylamine (MBHA) resin using manual SPPS in situ neutralization Boc chemistry protocols[40]. Peptide thioesters were prepared as described above and thioester formation relied upon a mercaptopropionic acid (MPA) strategy[41]. Side-chain protection for L-amino acids were as follows: Arg(Tos), Cys(4-MeBzl), Glu(OcHex), Lys(2-ClZ), and Thr(Bzl). The resins were washed with DCM and air dried after completion of stepwise SPPS. The peptides were simultaneously cleaved from the resin and side-chain deprotected by treatment with 10% (v/v) p-thiocresol and 10% (v/v) p-cresol in anhydrous HF for 1 hr at 0° C. Peptides were then triturated with cold diethyl ether, dissolved in 50% H2O:50% acetonitrile containing 0.1% TFA and lyophilized. These same solvent compositions were used in most experiments and will be referred to as A: 0.1% TFA in H2O and B: 0.1% TFA in acetonitrile.

Peptide Purification:

The crude peptides were dissolved in 95% A:5% B and purified by preparative RP-HPLC (Agilent Zorbax SB $C_{18}$ column: 21.2×250 mm, 7 μm, linear gradient: 1-41% B over 80 min, flow rate: 10 mL/min). HPLC fractions were spotted with MALDI matrix alpha-cyano-4-hydroxycinnamic acid (CHCA) in 50% A:50% B and checked for correct molecular masses. The purity of fractions was confirmed by analytical RP-HPLC (Agilent C18 Zorbax SB column: 2.1×150 mm, 5 μm, gradient: 1-51% B over 12 min, flow rate: 0.5 mL/min). Analytical HPLC UV absorbance traces in this work were measured at 214 nm. Model peptides used in this investigation are as follows (includes SEQ ID NOs:66-76):

```
Sequence                    Observed (Da)   Calculated (Da; Mono.)

GGGGG-G-MPA-LR-CONH2        717.4 ± 0.5     717.35
GGGGG-F-MPA-LR-CONH2        807.6 ± 0.5     807.39
GGGGG-S-MPA-LR-CONH2        747.8 ± 0.5     747.36
GGGGG-L-MPA-LR-CONH2        774.0 ± 0.5     773.41
GGGGG-MPA-LR-CONH2          660.3 ± 0.5     660.33
GGGG-MPA-LR-CONH2           603.8 ± 0.5     603.30
GGG-MPA-LR-CONH2            547.0 ± 0.5     546.28
GG-MPA-LR-CONH2             490.2 ± 0.5     489.26
G-MPA-LR-CONH2              433.3 ± 0.5     432.24
GGGGG-SGRELERG-MPA-LL-CONH2 1501.8 ± 0.1    1501.74
GGGGG-sGrelerG-MPA-LL-CONH2 1501.8 ± 0.1    1501.74
KLPETGG-CONH2               701.1 ± 0.5     700.40
CFRALKAA                    879.8 ± 0.5     879.49
GGGGGLRL                    685.1 ± 0.5     684.39
```

MPA: 3-mercaptopropionic acid. Lower case letters represents d-amino acids.

Model Sortase Reaction with Wildtype (WT) SrtA

Yield Analysis with Different $G_5$-Xaa-COSR

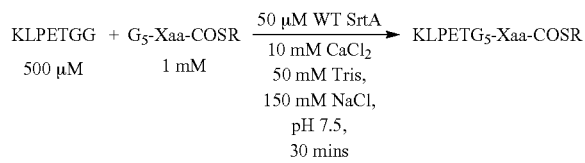

Xaa = Gly, Phe, Ser or Leu

For wild type (WT) sortase-mediated ligations, the substrate KLPETGG (SEQ ID NO:50) (500 μM) was incubated with $G_n$-Xaa-COSR (1 mM) in the presence of 50 μM WT sortase A (SrtA) in sortase buffer (10 mM $CaCl_2$, 50 mM Tris, 150 mM NaCl), pH 7.5 for 2 hours at room temperature. The reaction mixture was then quenched with equal volume of 50% A:50% B. The crude product yield was analyzed using RP-HPLC (Agilent Zorbax SB $C_{18}$ column: 2.1×150 mm, 5 μm, linear gradient: 1-61% B over 15 min, flow rate: 0.5 mL/min. The same analytical HPLC method has been used to analyze peptide sortagging reaction unless otherwise stated). The yield was calculated by manual integration of area under the curve for KLPETGG (SEQ ID NO:50) ($t_R$: 7.2 min). All experiments were performed in triplicate.

TABLE S1

Percentage yield for WT SrtA mediated ligations for $G_5$-Xaa-COSR (SEQ ID NO: 5) thioesters (Xaa = Gly, Phe, Ser or Leu) with 500 μM KLPETGG (SEQ ID NO: 50).

| Xaa | Gly | Phe | Ser | Leu |
|---|---|---|---|---|
| Yield (%) | 54(4) | 69(3) | 67(3) | 68(1) |

Kinetic Analysis of WT SrtA:

The substrate KLPETGG (SEQ ID NO:50) (500 μM) was incubated with $G_5$F-COSR (SEQ ID NO: 5) (500 μM) in the presence of 50 μM WT SrtA at room temperature in sortase buffer, pH 7.5. The reaction mixture was quenched with 20 μl of 50% A:50% B at time (in minutes)=1, 5, 10, 15, 20, 30, 40, 50, 60, 80, 100, and 120. The formation of product was analyzed using RP-HPLC via manual integration to obtain area under curve for the product peak ($t_R$: 12.6 min).

Kinetic analysis of SrtA*: The substrate KLPETGG (SEQ ID NO:50) (500 μM) was incubated with $G_5$F-COSR (SEQ ID NO:5) (500 μM) in the presence of 5 μM SrtA* at room temperature in sortase buffer, pH 7.5. The reaction was quenched with 20 μl of 50% A:50% B at time (in minutes) =1, 5, 10, 15, 20, 30, 40, 50, and 60. The product yield was analyzed using RP-HPLC and then manually integrated to obtain area under curve for the product peak ($t_R$: 12.6 min).

Sortase Reaction Followed by NCL with Model Peptide: SrtA* Mediated Ligation Followed by Purification

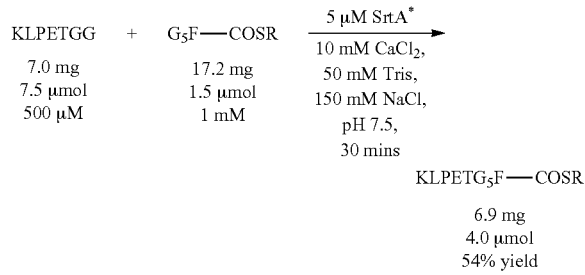

KLPETGG (SEQ ID NO:50) (7.0 mg, 7.5 μmol, 500 μM) was reacted with $G_5F$-COSR (17.2 mg, 15 μmol, 1 mM) with 5 μM SrtA* at room temperature for 30 minutes in sortase buffer, pH 7.5. The reaction was quenched with an equal volume of 95% A:5% B. The product KLPETG$_5$F-COSR (SEQ ID NO:77) was purified by preparative RP-HPLC (Agilent Zorbax SB $C_{18}$ column: 21.2×250 mm, 7 μm, gradient: 1-41% B in 80 min, flow rate: 5 mL/min). Preparative RP-HPLC fractions were analyzed using MALDI mass spectrometry, analytical RP-HPLC (Agilent Zorbax SB $C_{18}$ column: 2.1×150 mm, 5 μm, linear gradient: 1-51% B over 12 min, flow rate: 0.5 mL/min) and LCMS (Agilent Zorbax 300SB $C_3$ column: 2.1×150 mm, 5 μm, linear gradient: 1-61% B' over 15 min, flow rate: 0.4 mL/min. For LCMS we used solvent A': 0.1% formic acid in $H_2O$ and solvent B': 0.1% formic acid in acetonitrile. This same solvent system was used for all LCMS performed during the course of this work. Fractions containing the purified target peptide were combined and lyophilized to give 6.9 mg, 4.0 μmol of product (54% yield). The observed mass was 1285.7±0.1 Da (calculated monoisotopic mass: 1285.73 Da).

Native Chemical Ligation

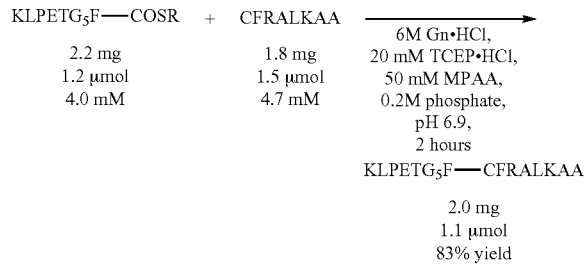

KLPETG$_5$F-COSR (SEQ ID NO:77) (2.2 mg, 1.2 μmol, 4.0 mM) was reacted with CFRALKAA (SEQ ID NO:75) (1.8 mg, 1.5 μmol, 4.7 mM) for 2 hours at room temperature in 6 M guanidine hydrochloride (Gn.HCl), 20 mM tris (carboxyethyl)phosphine hydrochloride (TCEP.HCl), 50 mM 4-mercaptophenylacetic acid (MPAA), 0.2 M potassium phosphate, at pH 6.9. The reaction mixture was quenched with an equal volume of 95% A:5% B. The product KLPETG$_5$F-CFRALKAA (SEQ ID NO: 79) was purified using preparative RP-HPLC (Agilent Zorbax SB $C_{18}$ column: 21.2×250 mm, 7 μm, linear gradient: 1-61% B over 120 min, flow rate: 5 mL/min). Preparative RP-HPLC fractions were then analyzed using MALDI mass spectrometry, analytical RP-HPLC (Agilent Zorbax SB $C_{18}$ column: 2.1×150 mm, 5 μm, linear gradient: 1-51% B over 12 min, flow rate: 0.5 mL/min) and LCMS (Agilent Zorbax 300SB $C_3$ column: 2.1×150 mm, 5 μm, linear gradient: 1-61% B' over 15 min, flow rate: 0.4 mL/min). Fractions containing the purified target peptide were combined and lyophilized to give 2.0 mg, 1.1 μmol (83% yield). The observed mass for product is 1880.0±0.1 Da (calculated monoisotopic mass: 1880.04 Da).

Protein Studies

Construction of Plasmids:

pET SUMO His$_6$-SUMO-eGFP-LPSTGG-His$_6$ (SEQ ID NO:80) was prepared by use of the Champion pET SUMO protein expression system (Invitrogen, CA). AccuPrime Taq DNA polymerase (Invitrogen, CA) was used to PCR amplify eGFP and the LPSTGG (SEQ ID NO:62) tag was added by using 5'-ATGGTGAGCAAGGGCGAGGAGCTGTTCAC-CGGGGTGGTGCCCATCCTGG-3' (forward) (SEQ ID NO: 81) and 5'-CTAATGGTGGTGGTGGTGGTGGC-CGCCGGTGCTCGGCAGCTTGTACAGCTCGTC-CATGC-3' (reverse) primers (SEQ ID NO:82). The product was confirmed by 1% (w/v) agarose gel electrophoresis and subsequently PCR purified by the QIAquick PCR purification kit (Qiagen, Netherlands). The PCR product was then cloned into pET SUMO by an overnight ligation at 15° C. with 6 ng PCR product, 25 ng pET SUMO vector, and 0.5 μl T4 DNA ligase. 2 μl of the ligation product was transformed into One Shot Mach1-T1 competent cells and plated on 30 μg/mL kanamycin plates and incubated overnight at 37° C. Colonies were grown in LB media containing 30 μg/mL kanamycin. The plasmid DNA was isolated using the Qiaprep spin miniprep kit (Qiagen, Netherlands). Glycine at position 2 in SUMO vector was mutated to isoleucine in all model proteins in order to prevent SrtA*-mediated intramolecular cyclization. These mutations were introduced using QuikChange Lightening Multi Site-Directed Mutagenesis Kit (Agilent, CA) with a 5'-GAAGGAGATATACATAT-GatCAGCAGCCATCATCATCATC-3' primer (SEQ ID NO: 83). The SrtA$_{59\text{-}206}$ construct employed in this study is a truncated version of naturally occurring SrtA in which the N-terminal membrane-spanning domain has been removed. The remaining portion of SrtA exhibits greater solubility in aqueous solution as consequence of membrane-spanning domain excision yet retains full catalytic activity.[3] SrtA* (P94S/D160N/K196T), evolved by Chen et al[4]., was prepared from WT SrtA in a pET 21 vector using a QuikChange Lightning Site-Directed Mutagenesis Kit (Agilent, CA). The following primers were used for the QuikChange (SEQ ID NOs: 84-86):

```
P94S:
5'-CCAGGACCAGCAACAtccGAACAATTAAATAGAGGTG-3',

D160N:
5'-GTATAAAATGACAAGTATAAGAaacGTTAAGCCAACAGATGTAGAA
G-3'

K196T:
5'-GACAGGCGTTTGGGAAaccCGTAAAATCTTTGTAG-3'
```

Protein Expression:

Recombinant His$_6$-SUMO-LF$_N$-LPSTGG-His$_6$ (SEQ ID NOs: 87), His$_6$-SUMO-LF$_N$-DTA(C186S)-LPSTGG-His$_5$ (SEQ ID NOs: 88) and His$_6$-SUMO-Cys-DTA(C186S) were expressed at New England Regional Center of Excellence/Biodefense and Emerging Infectious Diseases (NERCE). His$_6$-SUMO-eGFP-LPSTGG-His$_6$ was overexpressed in E. coli BL21 (DE3) cells. Approximately 10 g of cell pellet was lysed by sonication in 50 ml of 50 mM Tris, 150 mM NaCl, pH 7.5 buffer containing 30 mg lysozyme, 2 mg DNAase I, and 1 tablet of Roche protease inhibitor cocktail. The suspension was centrifuged at 17,000 rpm for one hour to remove cell debris. The supernatant was loaded onto a 5 ml HisTrap FF crude Ni-NTA column (GE Healthcare, UK) and washed with 50 mL of 40 mM imidazole in 20 mM Tris, 150 mM NaCl, at pH 8.5. The protein was eluted from the column with buffer containing 500 mM imidazole in 20 mM Tris, 150 mM NaCl, pH 8.5. Imidazole was removed from proteins using a HiPrep 26/10 Desalting column (GE Healthcare, UK) into 20 mM Tris, 150 mM NaCl, pH 8.5. Purified proteins were analyzed using an Any kD Mini-PROTEAN TGX Precast Gel (Bio-Rad, CA).

In addition, the proteins were analyzed by LCMS to confirm their purity and molecular weight analyzed via high-resolution ESI-QTOF MS (Agilent 6520) (Table S2). The charge-state series of the species were deconvoluted using Agilent MassHunter Bioconfirm using maximum entropy setting (Agilent Zorbax 300SB $C_3$ column: 2.1×150 mm, 5 μm, linear gradient: 5-35% B' over 6 min, 35-45% B' over 20 min, 45-65% B' over 3 min, flow rate: 0.4 mL/min).

TABLE S2

Observed molecular masses of protein constructs when analyzed by LCMS (SEQ ID NOs: 80, 87, 88).

| Protein | Observed MW (Da) | Calculated MW (Da; average) |
|---|---|---|
| SrtA*-His$_6$ | 19214.6 ± 0.4 | 19214.5 |
| GB1-His$_6$-SrtA$^3$ | 25218.5 ± 0.4 | 25218.2 |
| His$_6$-SUMO-LF$_N$-LPSTGG-His$_6$ | 45289.3 ± 0.4 | 45289.8 |
| His$_6$-SUMO-LF$_N$-DTA-LPSTGG-His$_5$ | 66700.0 ± 0.4 | 66700.1 |
| Cys-DTA | 20840.1 ± 0.4 | 20840.1 |
| His$_6$-SUMO-eGFP-LPSTGG-His$_6$❖ | 41711.7 ± 0.4 | 41710.9 |

❖ The eGFP mass was first calculated from the native primary sequence and then 20 kD was subtracted for peptide backbone cyclization and oxidation to form the chromophore.

Sort-Tagging of Peptide Thioesters to Proteins Containing C-Terminal LPSTGG
All the reactants and products were analyzed via high-resolution ESI-QTOF MS (Agilent 6520) following protocol outlined in the previous section.

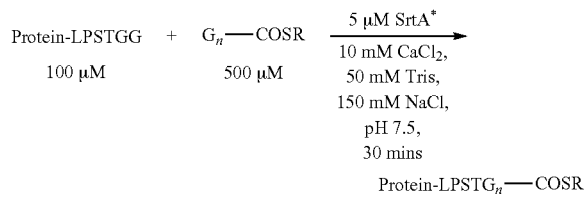

His$_6$-SUMO-Protein-LPSTGG-His$_{6/5}$ proteins (SEQ ID NO: 80) (100 μM) were incubated with $G_n$-COSR (500 μM) with 5 μM SrtA* for 30 min at room temperature (10 mM CaCl$_2$, 50 mM Tris, 150 mM NaCl, pH 7.5). The reaction mixture was then quenched with an equal volume of 50% A:50% B. The reaction was analyzed using LCMS (linear gradient: 5-35% B' over 6 min, 35-45% B' over 20 min, 45-65% B' over 3 min, flow rate=0.4 mL/min). All experiments were performed in triplicate. For all experiments, product formation was observed, but we were unable to determine the yield because the starting material and product co-eluted on LCMS. In addition, similar to peptide studies, for G-COSR, both protein-G-COSR and protein-GG-COSR were observed in products formed.

One-Pot SrtA* Mediated Preparation of Protein Thioesters

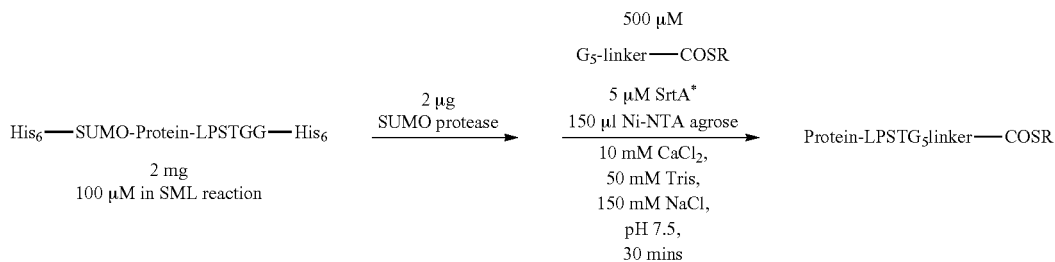

SUMO cleavage and SrtA* mediated ligation were conducted using a one-pot method. In particular, His$_6$-SUMO group on His$_6$-SUMO-protein-LPSTGG-His$_{6/5}$ (SEQ ID NO: 80) was cleaved first by incubating with 1 μg SUMO protease per mg protein at room temperature for 90 mins. The resultant mixture containing protein-LPSTGG-His$_{6/5}$ (100 μM) was reacted with G$_5$F-COSR (SEQ ID NO:49), G$_5$-SGRELER-COSR (SEQ ID NO: 89) G$_5$-sGreler-COSR (SEQ ID NO: 89) (500 μM) in the presence of 5 μM SrtA* and 150 μl of Ni-NTA slurry (Qiagen, Netherlands) for 30 min in buffer containing 10 mM CaCl$_2$, 50 mM Tris, 150 mM NaCl, pH 7.0. The His-tag free, ligated product (protein-LPSTG$_5$-linker-COSR) (SEQ ID NO:90) does not bind to Ni-NTA beads and was obtained by isolation of supernatant after centrifuging Ni-NTA agarose beads at 13,000 rpm for 1 min. Ni-NTA agarose beads were washed 3 times with 20 mM Tris, 150 mM NaCl, pH 7.0 buffer to capture residual product. The product was then concentrated using a Millipore centrifugal filter unit (10K) and washed 3 times with 20 mM Tris, 150 mM NaCl, pH 7.0 buffer to remove unreacted peptide thioesters. Yields are summarized in Table 3. We detected a small amount of thioester hydrolysis when the reactions were conducted at pH 7.5. The hydrolysis was eliminated when the experiments were performed at pH 7.0.

TABLE S3

Yield for SrtA* mediated synthesis of protein thioesters (SEQ ID NOs 1-3, 91-92).

| Protein | Thioester used | Starting Material (mg) | Protein-thioester (mg) | Yield (%) |
|---|---|---|---|---|
| eGFP | G$_5$F-COSR | 4.2 | 2.3 | 81 |
| LF$_N$-DTA | G$_5$F-COSR | 2.0 | 0.7 | 40 |
| LF$_N$ | G$_5$F-COSR | 2.3 | 0.6 | 50 |

TABLE S3-continued

Yield for SrtA* mediated synthesis of protein thioesters (SEQ ID NOs 1-3, 91-92).

| Protein | Thioester used | Starting Material (mg) | Protein-thioester (mg) | Yield (%) |
|---|---|---|---|---|
| $LF_N$ | $G_5$-L-linker-COSR | 2.3 | 0.7 | 50 |
| $LF_N$ | $G_5$-d-linker-COSR | 4.6 | 1.4 | 40 |

Native Chemical Ligation with eGFP Thioester eGFP—COSR + CFRALKAA
0.81 mg         0.5 mg
0.028 μmol    0.4 μmol
28 μM            4 mM → 20 mM TCEP·HCl, 10 mM MPAA, 0.2M phosphate, pH 7.0, 3 hours eGFP—CFRALKAA
0.80 mg
0.028 μmol
98% yield eGFP-LPSTG$_5$F-COSR (SEQ ID NO: 78) (0.81 mg, 0.028 μmol, 28 μM) was reacted with CFRALKAA (SEQ ID NO: 75) (0.5 mg, 0.4 μmol, 4 mM) for 3 hours in 20 mM TCEP.HCl, 10 mM MPAA, 0.2 M phosphate, pH 7.0. After 3 hours, the reaction mixture was concentrated with a Millipore centrifugal filter unit (10K) and washed three times with buffer (20 mM Tris, 150 mM NaCl, pH 7.0) to remove small molecule reactants (0.80 mg, 0.028 μmol, 98% yield).

Native Chemical Ligation with LFN-L-Linker-COSR and LFN-D-Linker-COSR to Cys-DTA:

$LF_N$-SGRELER-COSR (SEQ ID NO:93) (0.5 mg, 15 nmol, 0.2 mM) was reacted with Cys-DTA (1.4 mg, 66 nmol, 1 mM) for 7 hours in 20 mM TCEP.HCl, 10 mM MPAA, 0.2 M phosphate, pH 7.0. After 7 hours, the reaction mixture was diluted 5 times with 0.2 M phosphate buffer and 10 mM bromoacetamide was added to alkylate Cys on $LF_N$-L-linker-Cys-DTA. The alkylation reaction was quenched with 100 mM sodium 2-mercaptoethanesulfonate after 17 mins. $LF_N$-L-linker-DTA was isolated from the reaction mixture using HiLoad 26/600 Superdex 200 prep grade size exclusion chromatography column (GE Healthcare, UK) in 20 mM Tris, 150 mM NaCl, pH 7.5 buffer. Fractions containing pure product were concentrated with a Millipore centrifugal filter unit (10K). 0.16 mg of $LF_N$-L-linker-DTA (24 nmol, 20% yield) was obtained.

The D-peptide analogue $LF_N$-SGRELER-COSR (SEQ ID NO:93) (0.6 mg, 18 nmol, 0.2 mM) was reacted with Cys-DTA (1.4 mg, 66 nmol, 1 mM) under the same conditions as the L-peptide variant presented above. 0.065 mg of $LF_N$-D-linker-DTA (15.8 nmol, 7% yield) was obtained after size exclusion chromatography purification.

Figure 11A:
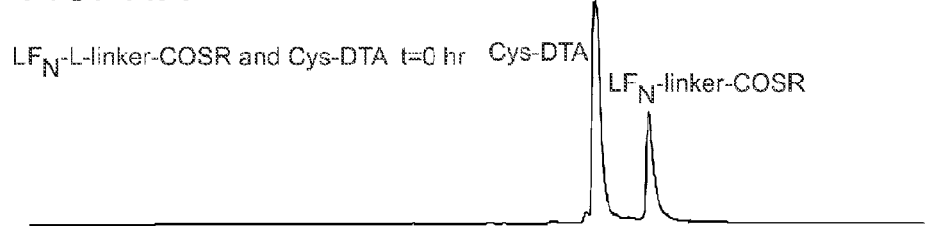
FIG. 11. LCMS data for native chemical ligation reaction between LF$_N$-L-linker and Cys-DTA. (a) at t=0 hr. (b) at t=5 hr. (c) purified alkylated LF$_N$-L-linker-DTA. The total ion current chromatogram is displayed. LCMS conditions: for (a) and (b), linear gradient: 5-65% B' over 15 min, flow rate=0.4 mL/min. for (c), linear gradient: 5-35% B' over 6 min, 35-45% B' over 20 min, 45-65% B' over 3 min, flow rate: 0.4 mL/min. The NCL reaction between LF$_N$-L-COSR and Cys-DTA is 80% complete after 5 hours. The NCL reaction for $LF_N$-D-linker-DTA precedes the same as $LF_N$-F-linker-DTA.
Figure 11B:
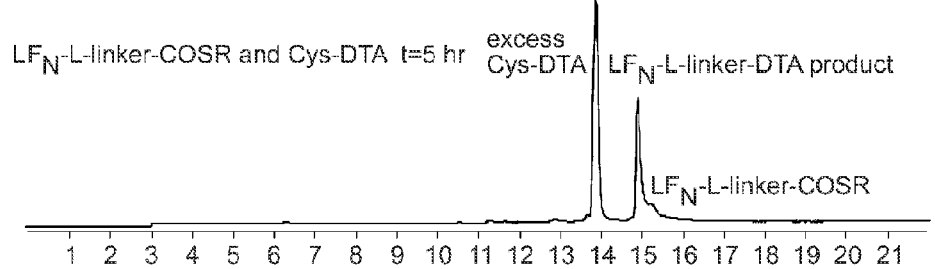
Figure 11C:
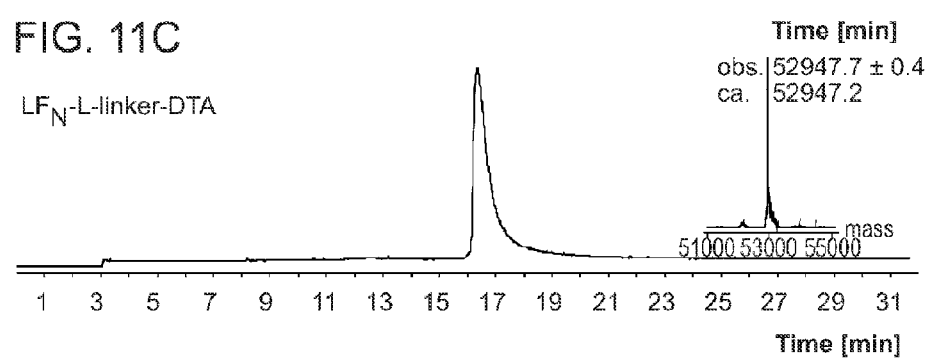

Through monitoring in LCMS, we observed near quantitative NCL reaction (FIG. 11). The unexpected low isolated yield has been attributed to loading a very small amount of protein on size exclusion column with 320 ml capacity, which lead to loss of product during purification.

Evaluation of LPSTGG Hydrolysis at Varying Concentrations of G5 Nucleophile:

To investigate the effect of $G_5$ nucleophile concentration on the extent of hydrolysis byproduct formation during the sortagging reaction, eGFP-LPSTGGHis$_6$ (SEQ ID NO:94) (50 μM) was incubated with $G_5$LRL (SEQ ID NO: 95) (0, 10, 30, 50, 100, 300 or 500 μM) and 7.35 μM SrtA* for 30 min at room temperature (10 mM CaCl$_2$, 50 mM Tris, 150 mM NaCl, pH 7.5). The reaction mixture was then quenched with an equal volume of 50% A:50% B and analyzed via LCMS (linear gradient: 1-61% B' over 15 min, flow rate=0.4 mL/min). Formation of a hydrolysis byproduct was noticeable at $G_5$ concentrations lower than 300 μM. Selected LCMS traces are shown in FIG. 12.

Translocation of $LF_N$-DTA-COSR, $LF_N$-L-Linker-DTA and $LF_N$-D-Linker-DTA into Cells Using Anthrax Protective Antigen:

$LF_N$-DTA, $LF_N$-L-linker-DTA, $LF_N$-D-linker-DTA and $LF_N$-DTA-LPSTG$_5$F-COSR (SEQ ID NO:96) were prepared at varying concentrations in 50 μL of F-12 media supplemented with 10% (v/v) fetal bovine serum, then 50 μL of F-12 media containing 10 nM protective antigen ($PA_{83}$) was added and mixed. Then 100 μl samples were added to CHO-K1 cells in 96-well plate and incubated for 30 minutes at 37° C. and 5% $CO_2$. The medium was then removed, washed 3 times with PBS, replaced with leucine-free F-12 medium supplemented with 1 μCi/mL $^3$H-Leu, and incubated for 1 hr at 37° C. 5% $CO_2$. The cells were washed 3 times with PBS and then 150 μL of scintillation fluid was added. The inhibition of protein synthesis by $LF_N$-DTA was determined by measuring $^3$H-Leu incorporation into cellular proteins. The scintillation counts were normalized to control value with PA only in the media. Each experiment was done in triplicate. The data were then plotted using Origin8 using Sigmoidal Boltzmann Fit using equation $$y = A2 + \frac{A1 - A2}{1 + e^{\frac{x - x_0}{dx}}}$$

where $x_0$ represents the log $EC_{50}$ values.

Results

We prepared variants of an oligoglycine $^{\alpha}$thioester and carried out model studies with peptide KLPETGG (SEQ ID NO:50). During the initial stages of our studies Chen et al. reported an evolved SrtA (SrtA*) that had improved enzymatic kinetics.[26] Once we confirmed SrtA* and SrtA gave similar product yield in model peptide studies, we chose to work exclusively with SrtA* because it substantially shortened reaction time. Reactions with SrtA* were complete in 30 minutes as opposed to 2 hours with SrtA (FIG. 5-6). The analytical RP-HPLC traces for a model reaction between KLPETGG (SEQ ID NO:50) and $G_5$F-COSR (SEQ ID NO:1-3) in the presence of SrtA* are shown in FIG. 1. We used RP-HPLC to purify the sortagged reaction product (6.9 mg, 54% yield) and then performed an NCL reaction under standard conditions. After purification, the NCL product was isolated (83% yield, 2 mg) and characterized by high resolution LCMS (FIG. 1*b*-*d*). We conducted additional sortagging studies to investigate two aspects of the oligoglycine $^{\alpha}$thioester: varying the C-terminal amino acid (Xaa) or varying the number of glycine residues. It has been demonstrated that the reactivity of a peptide $^{\alpha}$thioester is dependent upon the identity of the C-terminal amino acid; Gly is more reactive than Leu, for instance.[27,28] Product yields determined from analytical RP-HPLC ranged from 54-68% with SrtA (Table S1) and 74-84% with SrtA* (Table 1) suggesting the C-terminal amino acid Xaa does not significantly affect the reaction yield. We next investigated the relationship between reaction yield and the number of N-terminal glycine residues. The best yields were obtained when three or more glycines were used (Table 2).

TABLE 1

SrtA*-mediated ligation reaction yields with different G5-Xaa-COSR to model peptide

| Xaa | Gly | Phe | Ser | Leu |
|---|---|---|---|---|
| Yield (%) | 76(2) | 84(3) | 74(3) | 75(2) |

Reagents and conditions: 500 μM KLPETGG (SEQ ID NO:50) was reacted with 1 mM G$_5$-Xaa-COSR (SEQ ID NO:2) for 30 min in the presence of 5 μM SrtA* and SrtA* buffer (10 mM CaCl$_2$, 50 mM Tris, 150 mM NaCl) pH 7.5. The thioester R group was —CH$_2$—CH$_2$-L-R—CONH$_2$. Standard deviations are shown in parentheses.

TABLE 2

SrtA*-mediated ligation reaction yields with increasing number of glycines in G$_n$-COSR to model peptide.

| | Number of Gly | | | | | |
|---|---|---|---|---|---|---|
| | 1 | 2 | 3 | 4 | 5 | 6 |
| Yield(%) | 62(1)❖ | 46(8) | 68(6) | 69(3) | 70(1) | 59(8) |

Reagents and conditions: 500 μM KLPETGG (SEQ ID NO:50) was reacted with 1 mM G$_n$-COSR for 30 min in the presence of 5 μM SrtA* and SrtA* buffer, pH 7.5. ❖: Both KLPETGG-COSR (SEQ ID NO:97) and KLPETG-COSR (SEQ ID NO:98) were formed when G-COSR was used as the nucleophile. The yield represents the sum of both reactions.

With the ability to sortag oligopeptide $^\alpha$thioesters to peptides bearing a C-terminal acceptor sequence, we carried out investigations with three different model proteins. We prepared variants of eGFP, lethal factor N-terminal domain (LF$_N$) from anthrax toxin,[29] and lethal factor N-terminal domain fused to diphtheria toxin A-chain (LF$_N$-DTA).[29,30] DTA is the catalytic domain from diphtheria toxin and catalyzes the ADP-ribosylation of elongation factor-2 within the cytosol thereby halting protein synthesis and causing cell death.[31,32] LF$_N$ and LF$_N$-DTA are moieties used to probe the molecular basis of anthrax toxin protein translocation.[33] We prefer to express proteins as SUMO-protein fusions because expression yields are enhanced and the native N-terminus is generated after removal of SUMO.

Figure 2A:
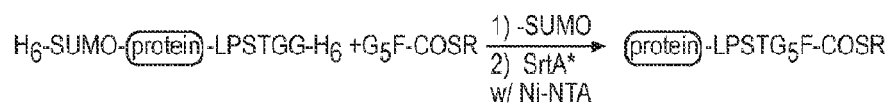
FIG. 2. LCMS data for protein $^\alpha$thioester synthesis using SrtA*. (a) SML of model proteins. (b)-(d) LCMS and deconvoluted MS (inset) of the main component for LF$_N$, LF$_N$-DTA and eGFP thioesters. Reaction conditions: (1) SUMO cleavage: 1 µg SUMO protease per 1 mg protein for 90 min at room temperature. (2) SML: 500 µM G$_5$F-COSR (SEQ ID NO:49), 100 µM protein-LPSTGG (SEQ ID NO:51), 5 µM SrtA*, 75 µl Ni-NTA agarose slurry per mg protein, SrtA* buffer, pH 7.0, 30 min. LCMS traces are shown as total ion current.
Figure 2B:
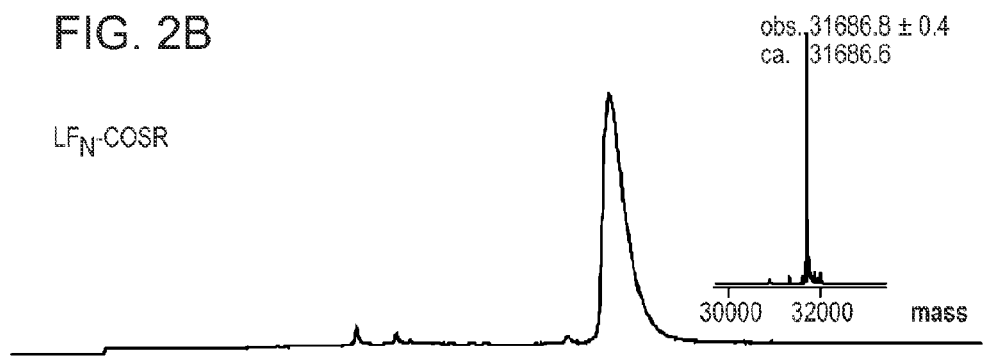
Figure 2C:
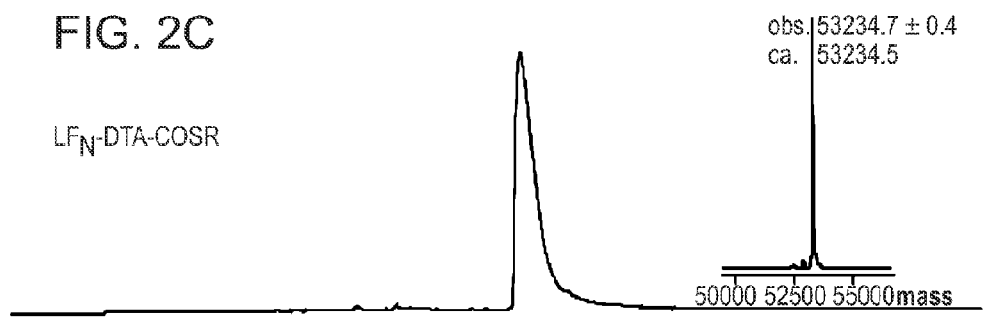
Figure 2D:
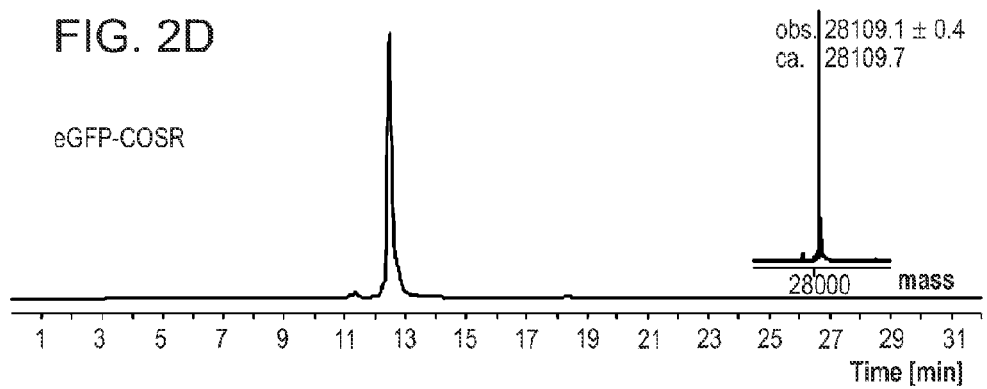
Figure 8A:
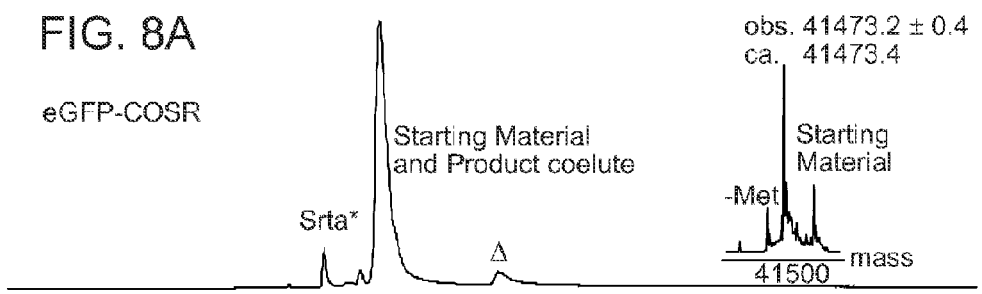
FIG. 8. Sample LCMS data for crude SrtA*-mediated ligation (SML) using G$_6$-COSR with the following model proteins: a) EGFP-COSR, b) LF$_N$-COSR and c) LF$_N$-DTA-COSR. The reactions were done in the absence of SUMO protease and Ni-NTA agarose. The total ion current chromatogram is displayed and the inset is the protein mass from the major peak after deconvolution. Δ: impurity in eGFP starting material.
Figure 8B:
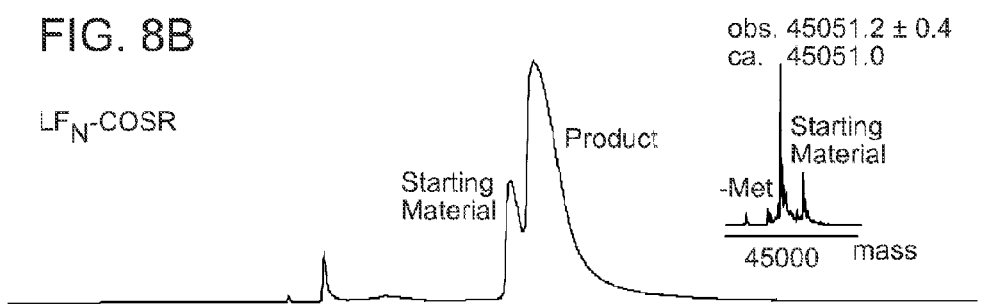
Figure 8C:
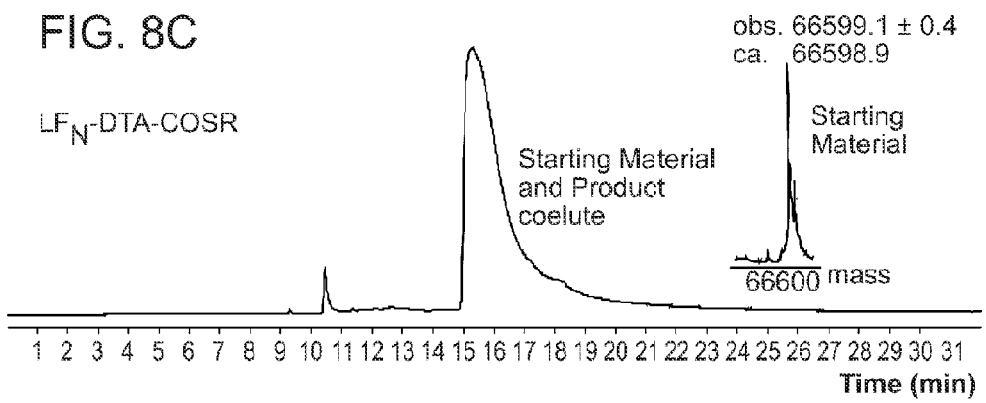
Figure 9:
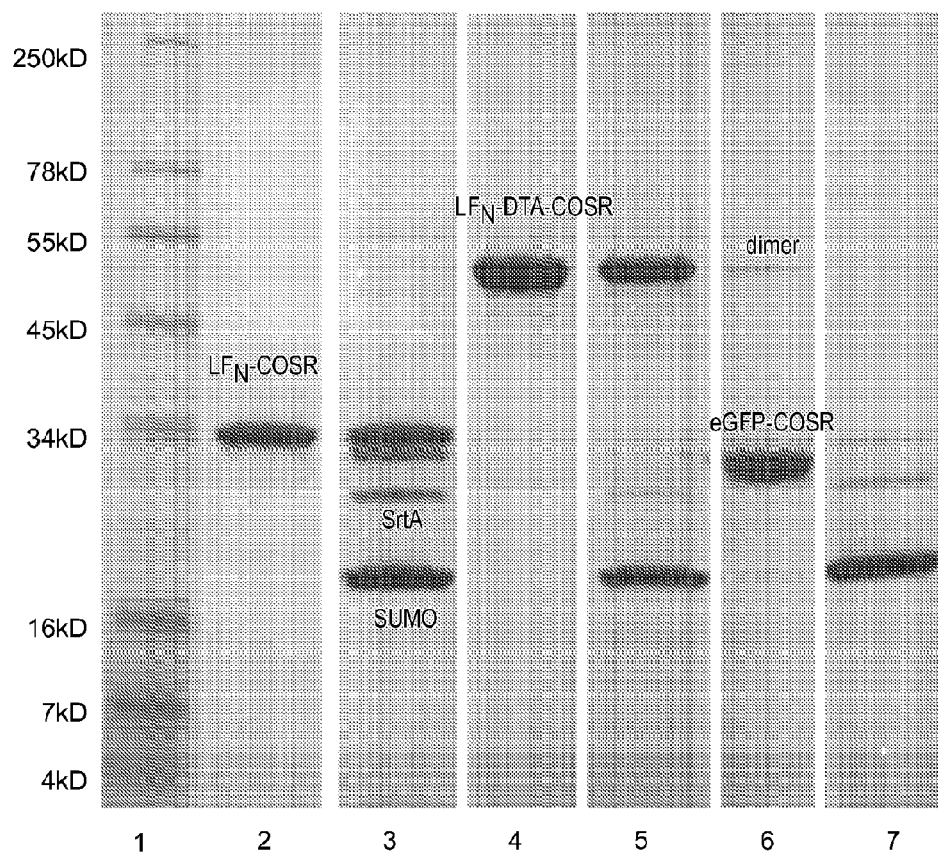
FIG. 9. Coomassie stained SDS-PAGE analysis of SrtA* mediated ligation in the presence of Ni-NTA agarose beads and SUMO protease. Lane 1: Invitrogen Seeblue@plus2 protein standard. Lane 2, 4, 6: LF$_N$-G$_5$F-COSR (SEQ ID NO:55), LF$_N$-DTA-G$_5$F COSR (SEQ ID NO:56), and eGFP-G$_5$F-COSR (SEQ ID NO:57). Lane 3, 5, 7: elute using 500 mM imidazole in 20 mM Tris, 150 mM NaCl, pH 8.5.
Figure 10:
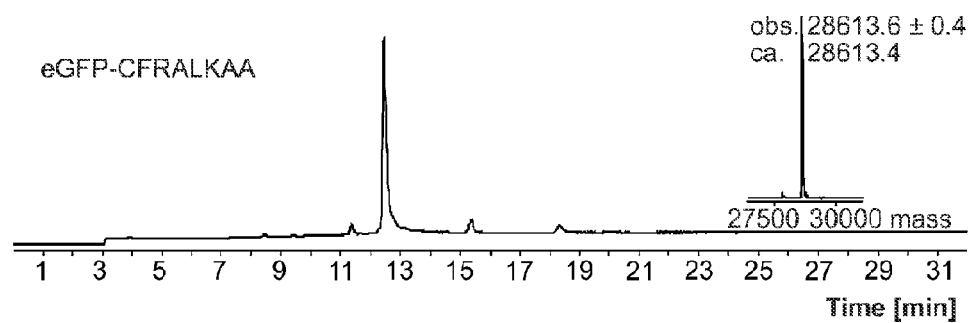
FIG. 10. LCMS data for native chemical ligation products of EGFP-CFRALKAA (SEQ ID NO:58). The total ion current chromatogram is displayed and the inset is the protein mass from the major peak after deconvolution.

We first investigated, by use of high resolution LCMS, whether SrtA* could tag thioesters onto our three different model proteins and found that protein thioester products are readily formed in 30 minutes (FIG. 8). We then proceeded to prepare protein thioesters on milligram scale using the approach shown in FIG. 2a. In particular, a one-pot method was employed whereby we first removed the N-terminal SUMO tag with SUMO protease and subsequently added SrtA*, Ni-NTA agarose beads, and oligoglycine $^\alpha$thioester peptide. After completion of the SrtA*-mediated ligation (SML) reaction, pure protein thioester was isolated by simple filtration and concentration because all unreacted material remained bound to the Ni-NTA agarose beads. We obtained good yields of pure protein $^\alpha$thioester and observed minimal amounts of SrtA-mediated hydrolysis when analyzed by high resolution LCMS (FIG. 2b-d). Our isolated yields for the three different model protein thioesters ranged from 40-80% (Table S3), which is consistent with prior reports for SML. When we monitored the sortagging reaction by SDS-PAGE and LCMS, we found some product still bound to the Ni-NTA agarose beads for LF$_N$ and LF$_N$-DTA but not eGFP (FIG. 9) suggesting the reaction yields are in part determined by the intrinsic properties of the protein. For eGFP-COSR we carried out NCL with the model peptide CFRALKAA (SEQ ID NO:75) under standard conditions (pH 7, TCEP, MPAA catalyst) and obtained 0.8 mg product (98% yield) (FIG. 10).[34]

Figure 3A:
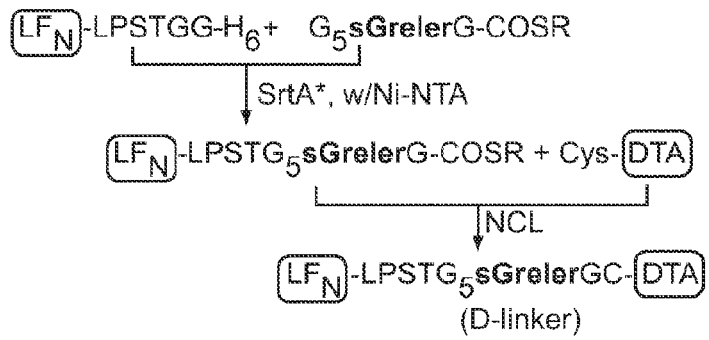
FIG. 3. Installing a D-peptide segment between LF$_N$ and DTA. (a) Synthetic strategy used to modify the linker region (lower case=D-amino acid). (b) LCMS and deconvoluted MS (inset) for LF$_N$-D-linker-DTA. The reaction conditions are reported in the supporting information. LCMS traces are shown as total ion current.
Figure 3B:
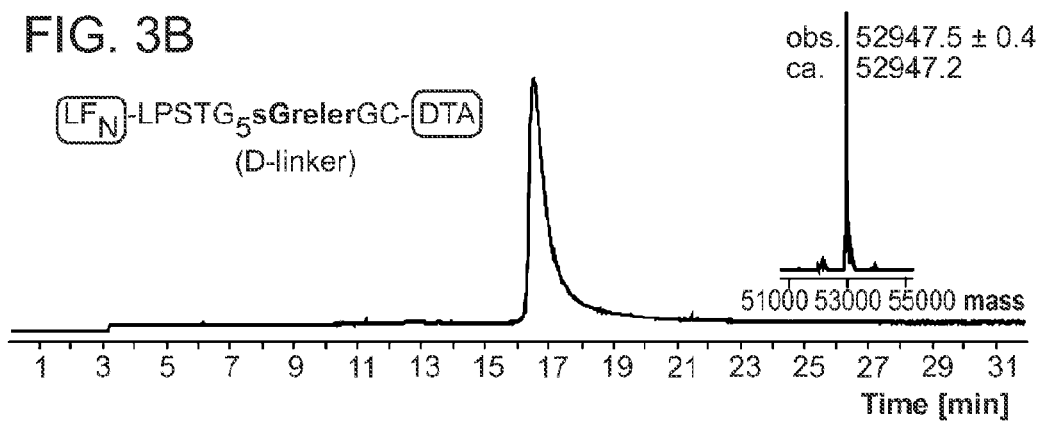

One of the proteins we have chosen to work with in these studies is LF$_N$-DTA. This chimera serves as an excellent model cargo protein to probe translocation through the anthrax toxin protective antigen (PA) pore. Having facile chemical access to this molecule allows for the incorporation of non-natural moieties to further elucidate the mechanisms in which this protein enters the cell through the PA pore. To begin these investigations, we aimed to study the translocation of LF$_N$-DTA-COSR and LF$_N$-D-linker-DTA, where "D-linker" refers to a small D-peptide tether between LF$_N$ and DTA. The preparation of these synthetic constructs is simplified by our new approach to generate protein thioesters. We prepared LF$_N$-D-linker-DTA using the approach shown in FIG. 3a. The synthetic approach involves first sortagging an oligoglycine thioester containing D-amino acids to LF$_N$ followed by NCL to ligate on the C-terminal DTA domain. We also prepared LF$_N$-L-linker-DTA using the same approach to serve as a control in our translocation assays (FIG. 11). By comparing the translocation efficiency of LF$_N$-D-linker-DTA against the L-amino acid variant, we were able to evaluate the stereochemical requirement for successful translocation through the pore.

Figure 4:
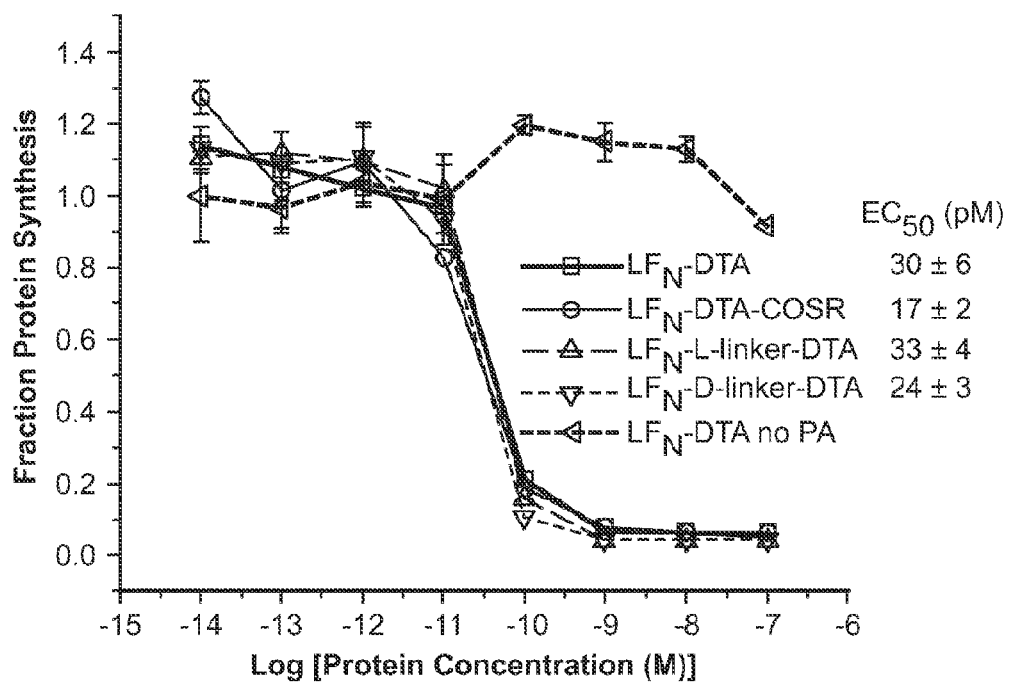
FIG. 4. Translocation of LF$_N$-DTA variants into CHO-K1 cells. Cells were incubated with LF$_N$-DTA, LF$_N$-DTA-COSR, LF$_N$-L-linker-DTA, or LF$_N$-D-linker-DTA at different concentrations in the presence or absence of 10 nM PA for 30 minutes. The media was then replaced with leucine-free medium supplemented with 1 µCi/mL $^3$H-Leu, and incubated for 1 hour. After incubation, the cells were washed three times with cold PBS, scintillation fluid was added, and incorporated $^3$H-Leu was determined by scintillation counting. Each data point represents the average of three trials at the specified concentration.
Figure 5:
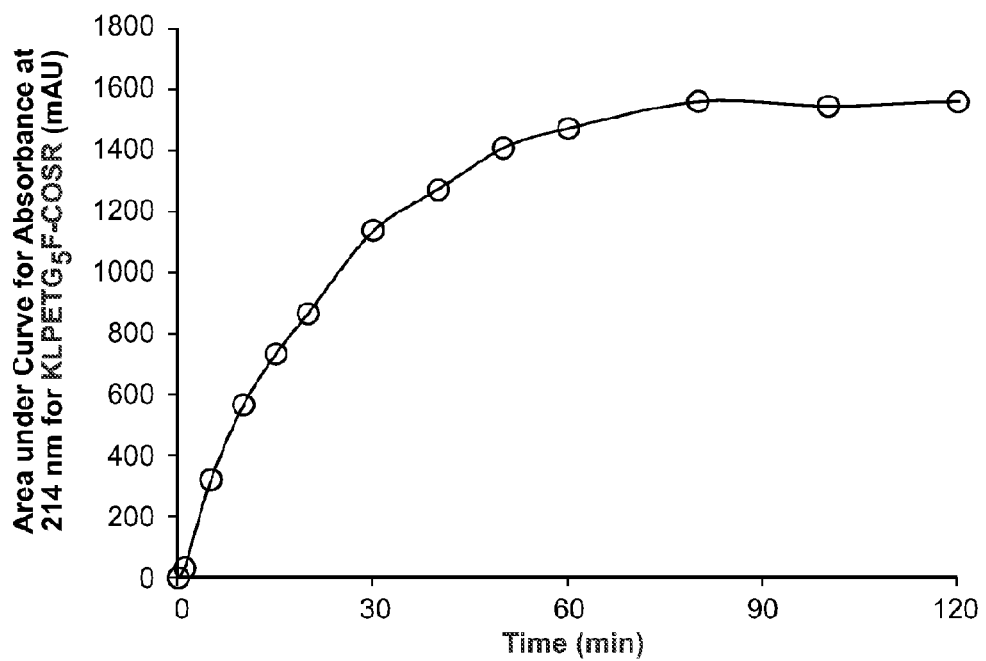
FIG. 5. Rate of product formation in the presence of WT SrtA.
Figure 6:
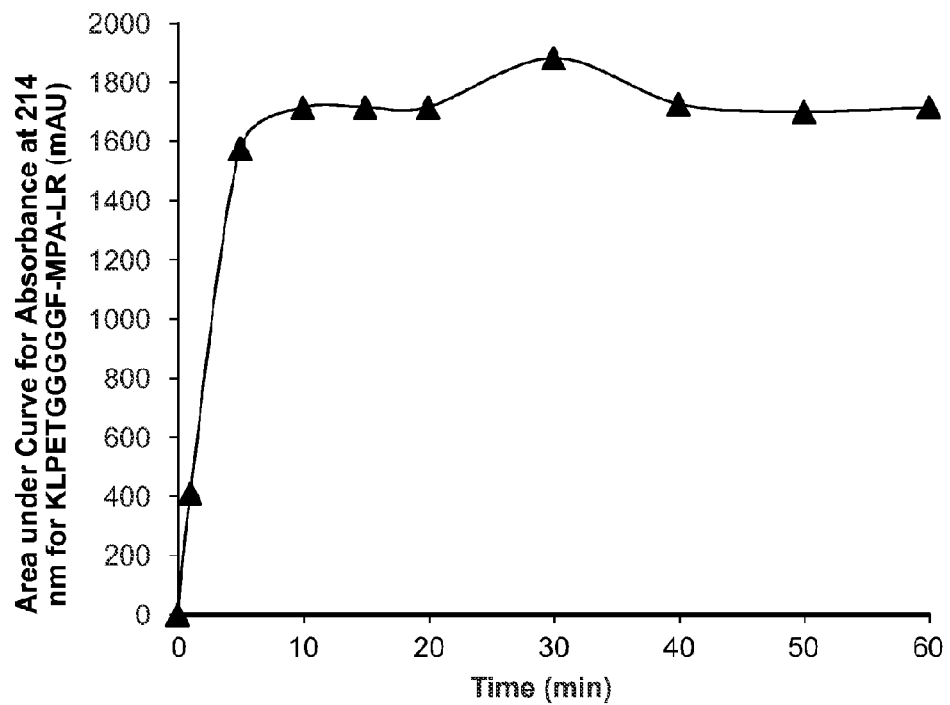
FIG. 6. Rate of product formation in the presence of SrtA*.
Figure 7:
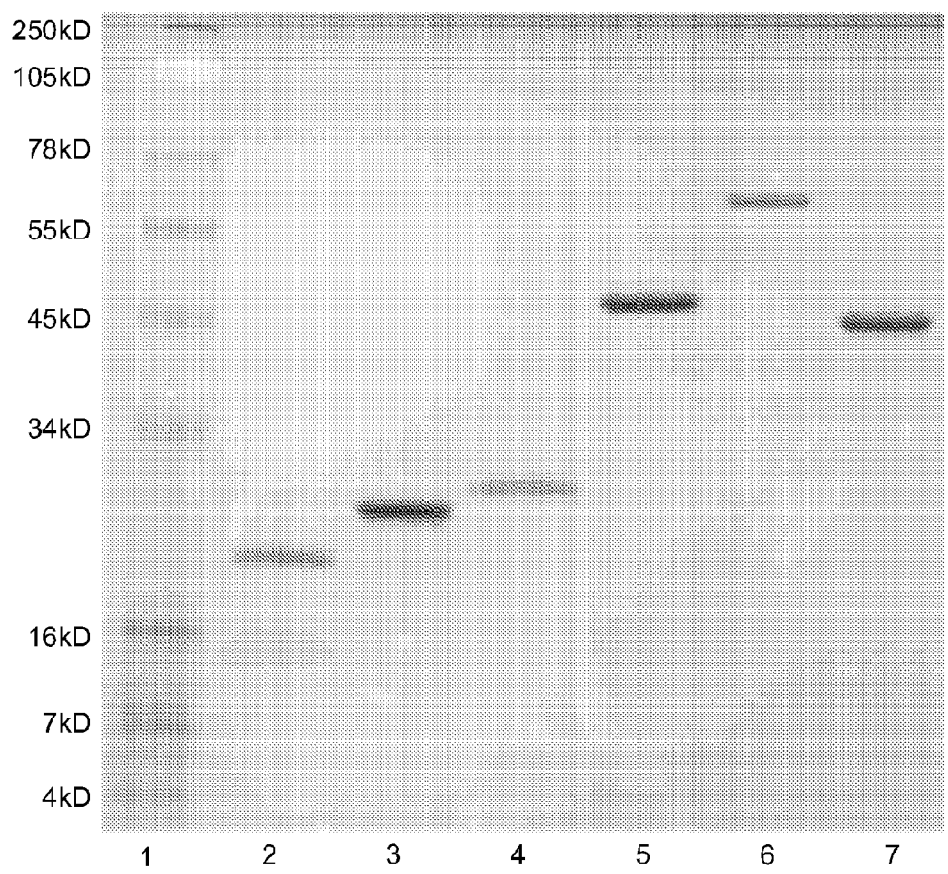
FIG. 7. Coomassie stained SDS-PAGE gel of protein constructs. Lane 1: Invitrogen Seeblue@plus2 protein standard. Lane 2: SrtA*-His$_6$. Lane 3: GB1-His$_6$-SrtA. Lane 4: His$_6$-SUMO protease. Lane 5: His$_6$-SUMO-LF$_N$-LPSTGG-His$_6$ (SEQ ID NO:52). Lane 6: His$_6$-SUMO-LF$_N$-DTA-LPSTGG-His$_6$ (SEQ ID NO:53). Lane 7: His$_6$-SUMO-EGFP-LPSTGG-His$_6$ (SEQ ID NO:54).

With our modified LF$_N$-DTA variants in hand, we tested if they could translocate through PA.[29] In this protein translocation assay, anthrax toxin PA and LF$_N$-DTA were added to CHO-K1 cells and the amount of LF$_N$-DTA delivered to the cytosol was inferred by measuring protein synthesis via $^3$H-Leu incorporation into the cellular proteome.[30,33] Once LF$_N$-DTA accesses the cytosol it inhibits protein synthesis. The protein synthesis levels for the variants are shown in FIG. 4. We found all variants to translocate at levels similar to wild-type LF$_N$-DTA.

Figure 23:
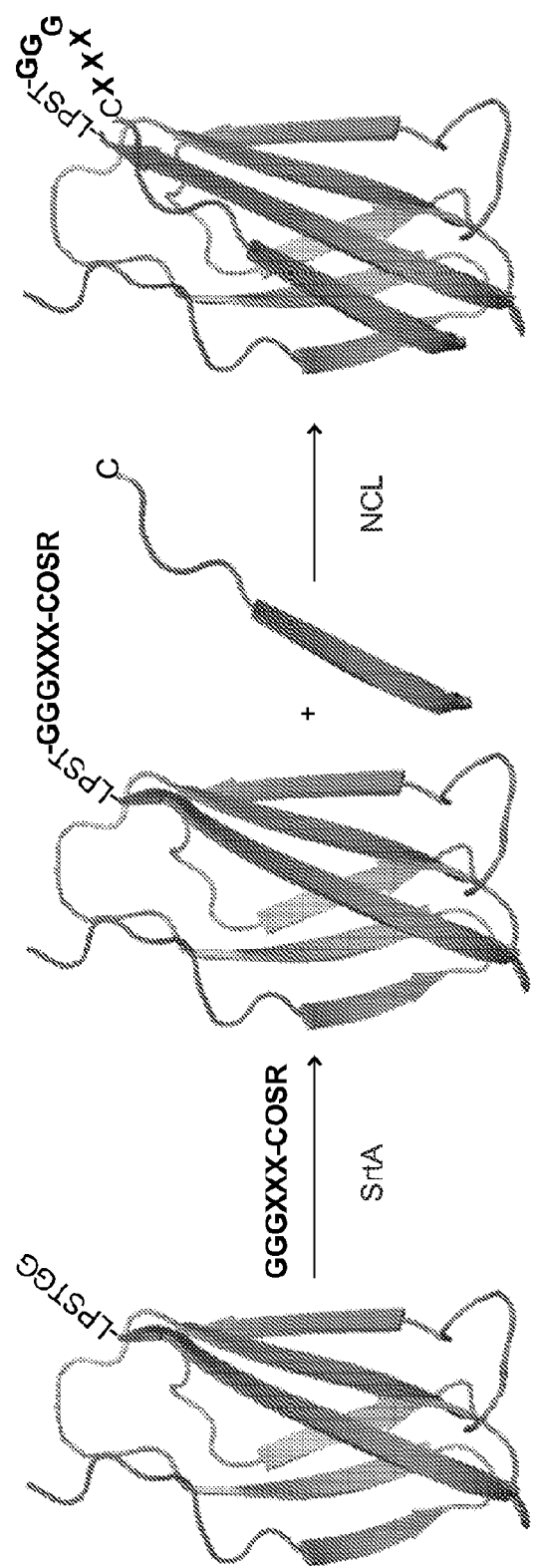
FIG. 23 is a schematic of the methods of the invention.

Example 2: A Method to Insert Non-Natural Amino Acids (NNAAs) into the Protein Loops The method is based on the fragment complementation property of many proteins and the double ligation assisted by Sortase A (SrtA) and native chemical ligation (NCL). A protein is split, normally at the flexible loop regions, into two fragments (N-terminal fragment A and C-terminal fragment B) that can complement and reassemble into stable and functional protein. An LPXTG (SEQ ID NO:61) tag and a Cysteine are incorporated at the C-termini of fragment A and the N-termini of fragment B, respectively. Fragment A undergoes SrtA mediated ligation with G$_5$-NNAAs-COSR (SEQ ID NO:99) peptide to generate fragment A-COSR product, which can then react with $^1$C-fragment B under complementation-assisted NCL. Given the loop regions are tolerant in elongation, the final product would result in a native fold with concomitant insertion of NNAAs (SEQ ID NO:100) in the loop. FIG. 23 shows a double ligation strategy for inserting NNAAs (X) into the FG loop of $_{10}$FN$_3$ We use the 10$^{th}$ human fibronectin type III domain ($_{10}$FN$_3$) and green fluorescent protein (GFP) for model study. $_{10}$FN$_3$ is dissected at FG loop into two fragments, AF and G. Fragment AF is expressed as SUMO fusion (SUMO-AF-LPSTGG) (SEQ ID NO:101) and $^1$C-fragment G ($^1$C-G) is synthesized by solid phase peptide synthesis. SUMO is first removed by SUMO protease to generate AF-LPSTGG (SEQ ID NO:102), which then react with G$_5$-COSR (SEQ ID NO:1) using SrtA. Following the generation of AF-LPSTG$_5$COSR (SEQ ID NO:103), $^1$C-G is added to the mixture to undergo NCL (FIG. 23). The product containing G$_5$ (SEQ ID NO:105) inserted in the FG loop of $_{10}$FN$_3$ (AF-G$_5$-G) (SEQ ID NO:105) is subsequently purified by anion-exchange column (FIG. 13). The circular dichroism spectrum of AF-G$_5$-G (SEQ ID NO:105) is similar to that of G$_{5-10}$FN$_3$ (SEQ ID NO:106), implying the product is correctly folded (FIG. 14). Similar results are obtained from fragment pairs of $_{10}$FN$_3$ dissected at BC loop or CD loop. The double ligations of fragment pairs of GFP at two different loops are under investigation.

Example 3: Flow Based Sortagging can be Performed at Low Nucleophile Concentrations To demonstrate the feasibility of flow-based sortagging at low nucleophile concentrations a model flow-based platform was designed that employed a protein substrate eGFP-LPSTGG-His$_6$ (SEQ ID NO:80), glycine nucleophile GGGG-LRL-CONH$_2$ (SEQ ID NO:107), and SrtA*-His$_6$ (FIG. 15A), where SrtA* is an optimized variant demonstrating improved reaction kinetics relative to wild-type SrtA. Next, a microreactor was constructed from a short segment of 0.020" HP-PFA tubing, a stainless-steel filter frit, a precolumn filter, and finger tight fittings. The outlet tubing of the microreactor was connected to a vacuum manifold and a slurry of Ni-NTA agarose beads pre-incubated with SrtA* enzyme (in sortase buffer) was drawn into the microreactor body. A syringe containing a mixture of 200 µg of eGFP-LPSTGG-His$_6$ and 20 µM G$_5$LRL in 800 µL sortase buffer (50 mM Tris, 150 mM NaCl, 10 mM CaCl$_2$, pH 8.2) was flowed through the SrtA* microreactor (hereafter referred to as the load fraction) at 65 µl/min via syringe pump. Subsequently, a syringe containing 1 mL of 20 µM G5LRL in sortase buffer (hereafter referred to as the push fraction) was similarly flowed through the microreactor to yield high purity material in good yield (FIG. 15B). His6 affinity tags on SrtA* and eGFP-LPSTGG-His$_6$ (SEQ ID NO:94) ensured that both proteins remained resin bound; only upon effective transpeptidation was the eGFP-LPST-G$_5$LRL (SEQ ID NO:108) ligation product released from the microreactor. LCMS analysis revealed that batch sortagging reactions provided minimal desired product (FIG. 15C). Ni-NTA treatment successfully removed unreacted starting material but major dimer formation was observed (FIG. 15D).

To compare the designed flow reactor to traditional batch chemistry a sortagging reaction was performed with the eGFP construct and a model peptide (50 µM eGFP-LPSTGG-His$_6$ (SEQ ID NO:94), 20 µM G$_5$LRL (SEQ ID NO:95), 3.5 µM SrtA*, sortase buffer, 20 min). To evaluate whether the desired ligation product (eGFP-LPST-G$_5$LRL) (SEQ ID NO:108) could be isolated via batch mode affinity purification, the reaction mixture was incubated with of Ni-NTA slurry (freshly buffer exchanged with sortase buffer) for 10 minutes on a nutating mixer. LCMS analysis revealed that batch sortagging reactions provided minimal desired product. Ni-NTA treatment successfully removed unreacted starting material but major dimer formation was observed (FIG. 15D).

Figure 16:
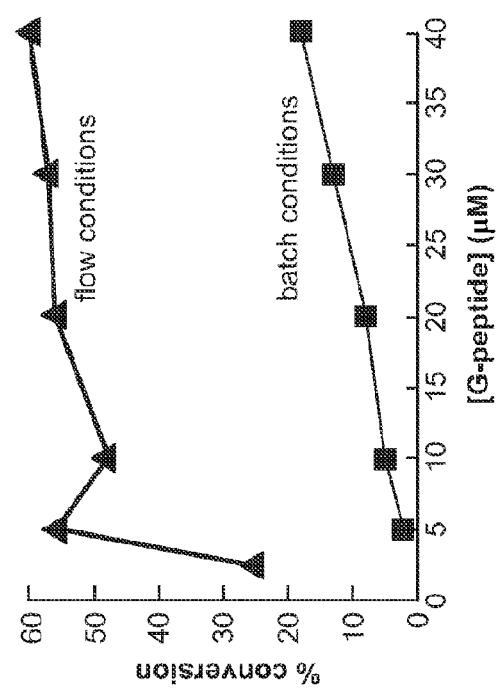
FIG. 16 is a graph demonstrating that ligation efficiency after flow sortagging reactions at low micromolar nucleophile was successful.

After flow sortagging reactions in the 20 uM nucleophile batch was successful, ligation efficiency was investigated by examining a range of G5LRL (SEQ ID NO:95) concentrations (2.5-40 µM). SML under continuous flow consistently yielded the desired ligation construct (eGFP-LPSTG$_5$LRL) (SEQ ID NO:108) with no impurities and at higher yields than comparative batch reactions (FIG. 16). While traditional sortagging reactions operate in the 300-500 µM nucleophile regime, high-efficiency ligation was observed at nucleophile concentrations in the 10-20 µM range for the sortase-mediated ligation with continuous flow.

Example 4: Reliable Bioconjugation with Different Protein Substrates

Figure 17A:
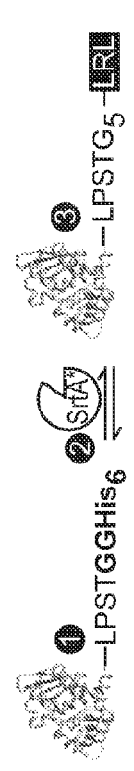
FIG. 17 depicts reliable bioconjugation with different protein substrates. The construct LFN-LPSTGG-His6 was expressed and purified via affinity chromatography and used to explore flow ligation between LFN-LPSTGG-His6 and G5LRL (20 μM) (FIG. 17A). High efficiency, high-purity ligation was observed as evidenced by the absence of side product or starting material contamination in the reactor flow-through (FIG. 17B). Comparatively, batch mode sortagging revealed minimal product formation and significant amounts of LFN-LPSTGG-His6 (SEQ ID NO:108) hydrolysis and cyclization (FIG. 17C). Post Ni-NTA treatment of the batch reaction demonstrated complete removal of unreacted LFN-LPSTGG-His6 (SEQ ID NO:108) but hydrolysis and cyclization byproducts were not removed because upon T-G bond cleavage they no longer contain a His6 affinity tag (FIG. 17D).
Figure 17B:
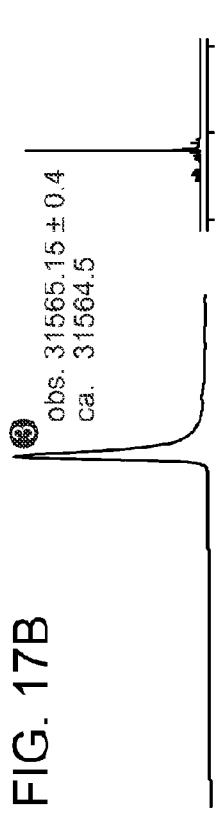
Figure 17C:
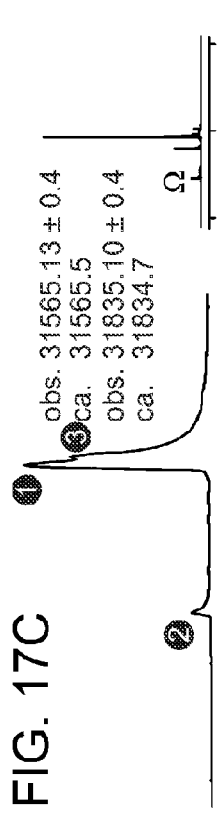
Figure 17D:
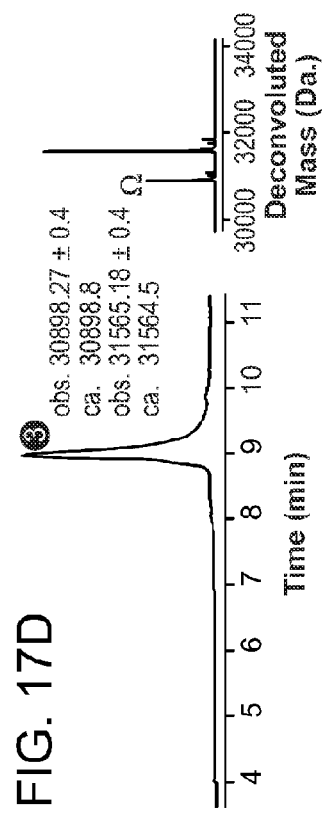

The eGFP flow experiments demonstrated reliable sortagging even at low micromolar nucleophile concentrations. To confirm that these observations were not protein specific, another sortagging substrate was studied: the anthrax toxin lethal factor N-terminal domain (LF$_N$). The construct LF$_N$-LPSTGG-His$_6$ (SEQ ID NO:108) was expressed and purified via affinity chromatography and used to explore flow ligation between LF$_N$-LPSTGG-His$_6$ (SEQ ID NO:108) and G$_5$LRL (SEQ ID NO:95) (20 µM). The construct LF$_N$-LPSTGG-His$_6$ was expressed and purified via affinity chromatography and used to explore flow ligation between LF$_N$-LPSTGG-His$_6$ and G$_5$LRL (20 µM) (FIG. 17A). Flow protocols identical to those used in model eGFP studies were utilized, with LF$_N$-LPSTGG-His$_6$ (SEQ ID NO:108 serving as the protein substrate instead of eGFP-LPSTGG-His$_6$ (SEQ ID NO:94). High efficiency, high-purity ligation was observed as evidenced by the absence of side product or starting material contamination in the reactor flow-through (FIG. 17B). The lower limit of necessary nucleophile concentration was probed by screening G$_5$LRL (SEQ ID NO:95) concentrations (2.5-40 µM). Flow reactions were compared to batch reactions between LF$_N$-LPSTGG-His$_6$ (SEQ ID NO:108) and G$_5$LRL (SEQ ID NO:95) (50 µM LF$_N$-LPSTGG-His$_6$, 20 µM G$_5$LRL, 3.5 µM SrtA*-His, sortase buffer, 20 min). Comparatively, batch mode sortagging revealed minimal product formation and significant amounts of LF$_N$-LPSTGG-His$_6$ (SEQ ID NO:108) hydrolysis and cyclization (FIG. 17C). Post Ni-NTA treatment of the batch reaction demonstrated complete removal of unreacted LF$_N$-LPSTGG-His$_6$ (SEQ ID NO:108) but hydrolysis and cyclization byproducts were not removed because upon T-G bond cleavage they no longer contain a His$_6$ affinity tag (FIG. 17D).

Example 5: Platform Efficiency with Different Glycine Nucleophiles

Figure 18A:
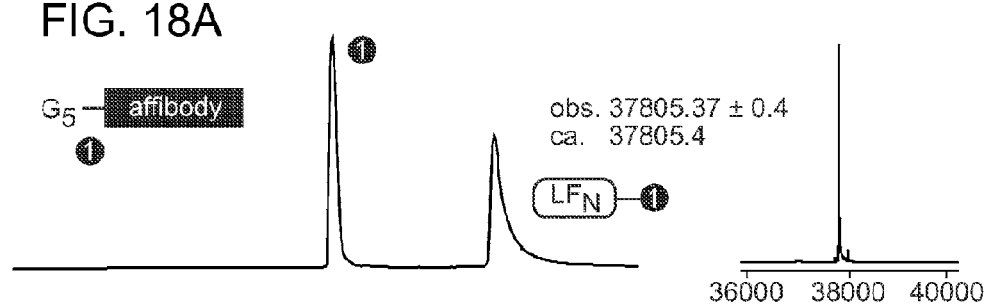
FIG. 18 demonstrates platform efficiency with different glycine nucleophiles. Protein substrate LFN-LPSTGG-His6 (SEQ ID NO:108) was subjected to flow based sortagging with protein nucleophile G5-affibody (SEQ ID NO:110) (MW 6925.6) to yield the desired conjugate LFN-LPSTG5-affibody (SEQ ID NO:111) in high purity and in good yield (FIG. 18A). Similarly, protein nucleophile G5-fibronectin3 (SEQ ID NO:106) (MW 11022.2) was employed to yield the desired construct LFN-LPSTG5-fibronectin3 (SEQ ID NO:113) in high purity and in good yield (FIG. 18B). Finally, peptide nucleophile G5-2Dpico (SEQ ID NO:112) (a relatively insoluble fluorine containing peptide) was successfully conjugated to form the desired LFN-LPSTG5-2Dpico (SEQ ID NO:114) (FIG. 18C).
Figure 18B:
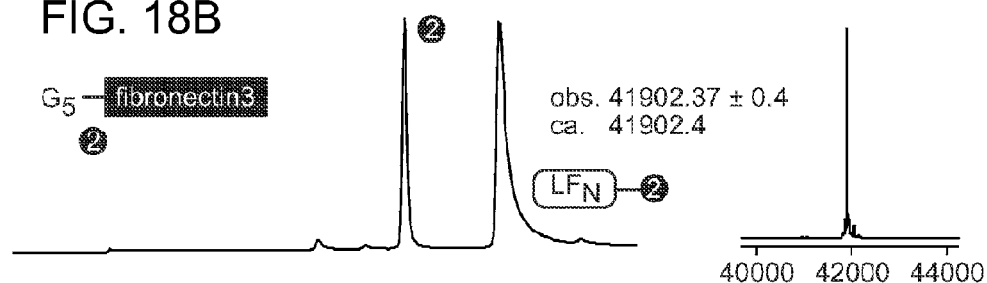
Figure 18C:
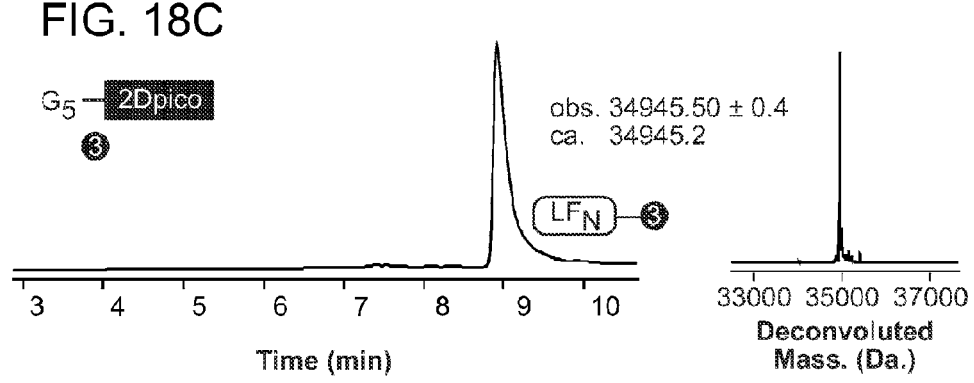

Having demonstrated the platforms expanded working range with glycine nucleophile concentrations and demonstrating reliable bioconjugation with different protein substrates, the efficiency of this platform with different glycine nucleophiles was evaluated. Two types of glycine nucleophiles: 1) protein nucleophiles and 2) nucleophiles with poor solubility have rendered sortagging challenging in certain circumstances. Protein substrate LF$_N$-LPSTGG-His$_6$ (SEQ ID NO:108) was subjected to flow based sortagging with protein nucleophile G$_5$-affibody (SEQ ID NO:110) (MW 6925.6) to yield the desired conjugate LF$_N$-LPSTG$_5$-affibody (SEQ ID NO:111) in high purity and in good yield (FIG. 18A). Similarly, protein nucleophile G$_5$-fibronectin3 (SEQ ID NO:106) (MW 11022.2) was employed to yield the desired construct LF$_N$-LPSTG$_5$-fibronectin3 (SEQ ID NO:113) in high purity and in good yield (FIG. 18B). Finally, peptide nucleophile G$_5$-2Dpico (SEQ ID NO:112) (a relatively insoluble fluorine containing peptide) was successfully conjugated to form the desired LF$_N$-LPSTG$_5$-2Dpico (SEQ ID NO:114) (FIG. 18C).

Example 6: Insertion of Synthetic Peptides into Protein Loops

The method uses a double ligation and concomitant protein fragment complementation to insert a synthetic peptide into protein loops. It is based on the fragment complementation property of many proteins. A protein is split, normally at the flexible loop regions, into two fragments that can complement and reassemble into stable and functional protein. We incorporate an LPSTGG (SEQ ID NO:62) tag and a Cysteine at the N-terminal fragment (N) and the C-terminal fragment (C), respectively. We use SrtA to attach (sortagging) a synthetic peptide thioester onto the N fragment, which can then react with the C fragment bearing an N-terminal Cysteine under complementation-assisted NCL. Given the loop regions are tolerant in elongation, the final product would result in a native fold with concomitant insertion of the synthetic peptide in the loop.

Figures 19A, 19B, 19C:
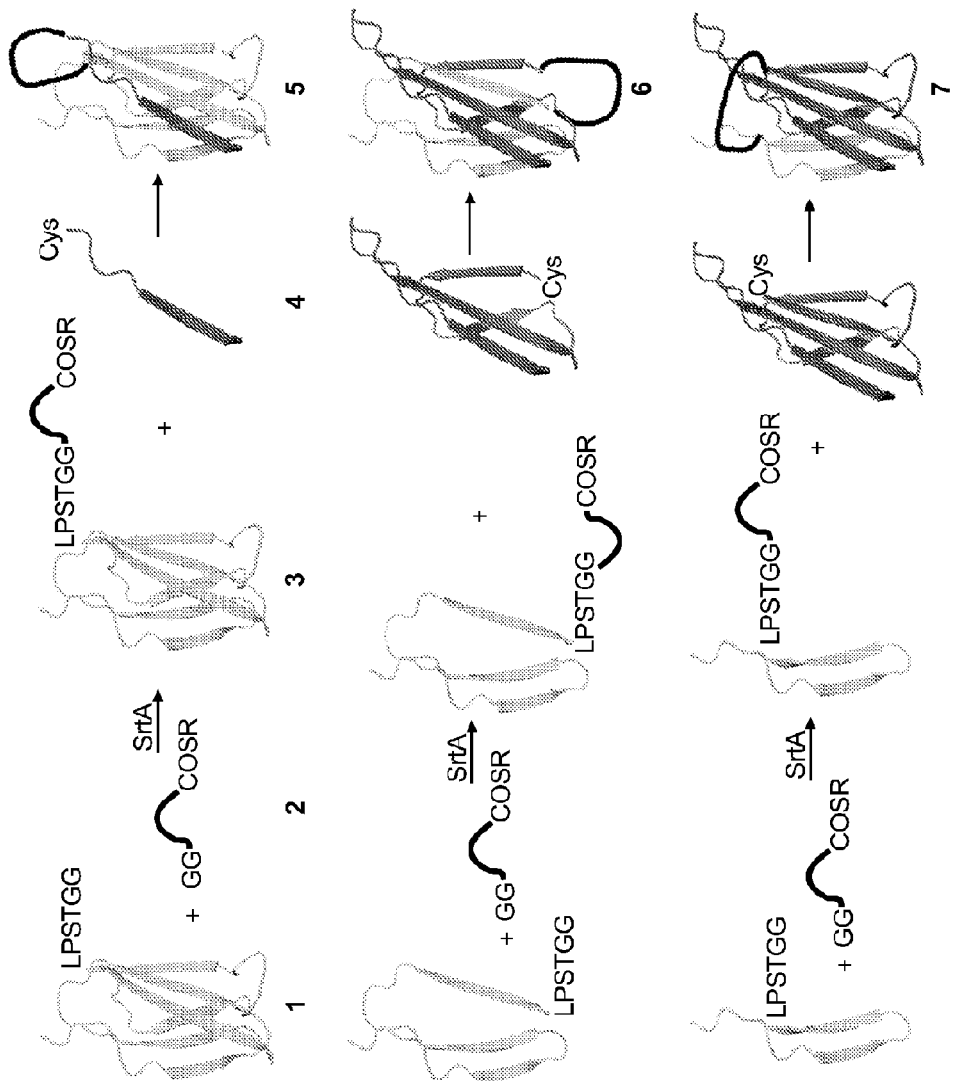
FIG. 19. Double ligation strategy for inserting synthetic peptides into the FG loop (a), CD loop (b), or BC loop (c) of $_{10}FN_3$. The N-terminal fragments are represent in lighter shading and the C-terminal fragments are represent in darker shading.

Studies were performed using the 10th human fibronectin type III domain ($_{10}FN_3$) for model study. $_{10}FN_3$ was dissected into two fragments at three different loops, FG loop, CD loop, and BC loop FIG. 19. The resulting fragments A-F, ABC, D-G, AB and C-G were expressed as SUMO fusions while fragment G were synthesized by solid phase peptide synthesis. In the case of $_{10}FN_3$ dissected at the FG loop, SUMO was the first removed by SUMO protease to generate A-F_LPSTGG (SEQ ID NO:115)(1), which then reacted with $G_5$-COSR (SEQ ID NO:1) (2) using SrtA (FIG. 20*a*). Following the generation of A-F_LPSTG$_5$COSR (SEQ ID NO:103) (3), fragment G (4) was added to the mixture to undergo NCL (FIG. 19*b*). The product containing $G_5$ was inserted in the FG loop of $_{10}FN_3$ (A-F_$G_5$_G) (SEQ ID NO:105) (5) was subsequently purified by anion-exchange column (FIG. 20*c*). In the case of $_{10}FN_3$ dissected at CD loop or BC loop, we conducted a one-pot double ligation using double-His-tagged N terminal fragments which reacted with $G_5$-COSR (SEQ ID NO:1) and C terminal fragments in the presence of SrtA and Ni-NTA. By simple washing and subsequent SUMO cleavage, we obtained the full-length protein with $G_5$ inserted at CD loop (6) or BC loop (7) from the supernatant without further purification (FIG. 20*e*).

Figure 21A:
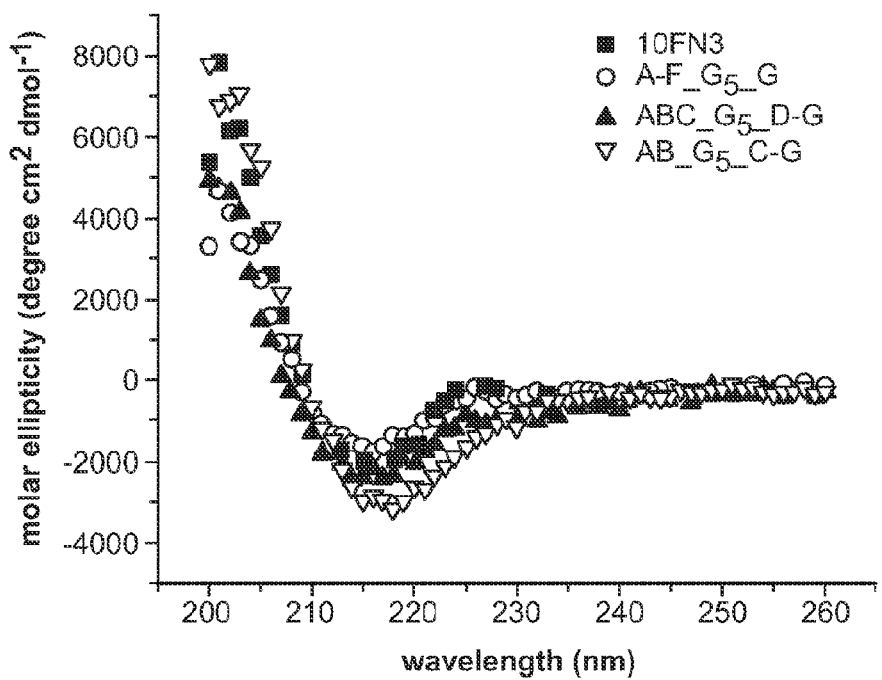
FIG. 21: Circular Dichroism spectra and thermal denaturation of $_{10}FN_3$ with G5 inserted at FG, CD and BC loop from double ligation reactions. The ellipticity at 216 nm was measured from 25° C. to 95° C.
Figure 21B:
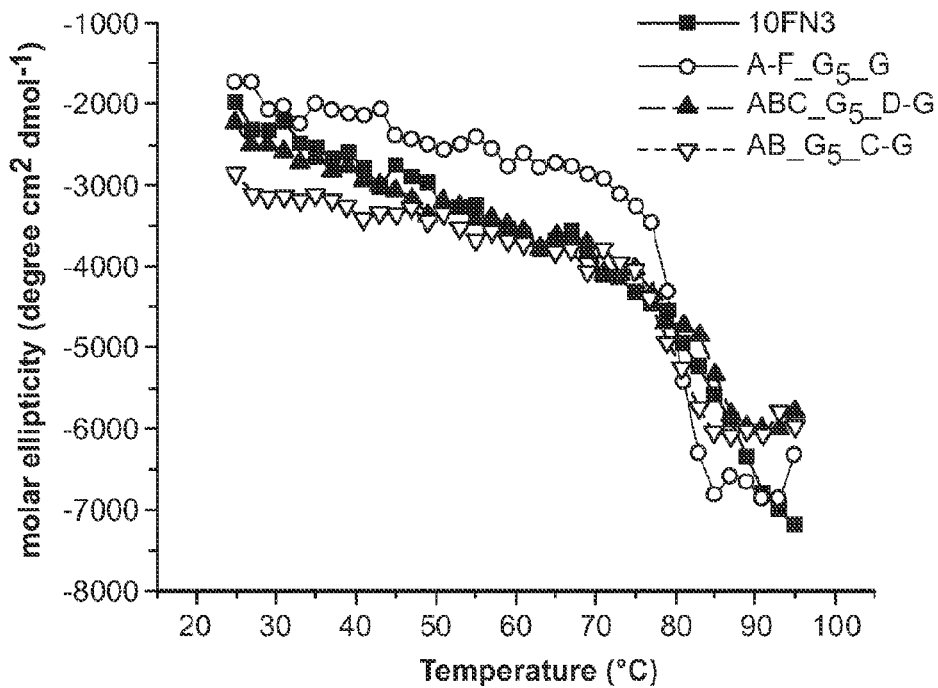

Circular dichroism was used to characterize the products from double ligation. As shown in FIG. 21*a*, all three products have similar CD spectra to that of wild-type $_{10}FN_3$, implying the products are correctly folded. Thermal denaturation monitored by CD indicated that the products have similar $T_m$ or thermal stability to that of wild-type $_{10}FN_3$ (FIG. 21*b*). The binding properties of $_{10}FN_3$ variants were fine-tuned by inserting different synthetic peptides in the loop regions.

REFERENCES (1) Murakami, M.; Okamoto, R.; Izumi, M.; Kajihara, Y. Angew. Chem. Int. Ed. Engl. 2012, 51, 3494.
(2) Nagorny, P.; Sane, N.; Fasching, B.; Aussedat, B.; Danishefsky, S. J. Angew. Chem. Int. Ed. Engl. 2012, 51, 975.
(3) Bavikar, S. N.; Spasser, L.; Haj-Yahya, M.; Karthikeyan, S. V.; Moyal, T.; Kumar, K. S.; Brik, A. Angew. Chem. Int. Ed. Engl. 2012, 51, 758.
(4) Vila-Perello, M.; Muir, T. W. Cell 2010, 143, 191.
(5) Scheuermann, J. C.; de Ayala Alonso, A. G.; Oktaba, K.; Ly-Hartig, N.; McGinty, R. K.; Fraterman, S.; Wilm, M.; Muir, T. W.; Muller, J. Nature 2010, 465, 243.
(6) Chatterjee, C.; McGinty, R. K.; Fierz, B.; Muir, T. W. Nat. Chem. Biol. 2010, 6, 267.
(7) Muir, T. W. Annu. Rev. Biochem. 2003, 72, 249.
(8) Kent, S. B. Chem. Soc. Rev. 2009, 38, 338.
(9) Dawson, P. E.; Muir, T. W.; Clark-Lewis, I.; Kent, S. B. Science 1994, 266, 776.
(10) Severinov, K.; Muir, T. W. J. Biol. Chem. 1998, 273, 16205.
(11) Muir, T. W.; Sondhi, D.; Cole, P. A. Proc. Natl. Acad. Sci. U.S.A. 1998, 95, 6705.
(12) Evans, T. C., Jr.; Benner, J.; Xu, M. Q. Protein. Sci. 1998, 7, 2256.
(13) Mazmanian, S. K.; Liu, G.; Ton-That, H.; Schneewind, O. Science 1999, 285, 760.
(14) Navarre, W. W.; Schneewind, O. Mol. Microbial. 1994, 14, 115.
(15) Wu, Z.; Guo, X.; Guo, Z. Chem. Commun. (Camb) 2011, 47, 9218.
(16) Popp, M. W.; Ploegh, H. L. Angew. Chem. Int. Ed. Engl. 2011, 50, 5024.
(17) Wu, Z.; Guo, X.; Wang, Q.; Swarts, B. M.; Guo, Z. J. Am. Chem. Soc. 2010, 132, 1567.
(18) Proft, T. Biotechnol. Lett. 2010, 32, 1.
(19) Clancy, K. W.; Melvin, J. A.; McCafferty, D. G. Biopolymers 2010, 94, 385.
(20) Yamamoto, T.; Nagamune, T. Chem. Commun. (Camb) 2009, 1022.
(21) Tsukiji, S.; Nagamune, T. Chembiochem 2009, 10, 787.
(22) Guo, X.; Wang, Q.; Swarts, B. M.; Guo, Z. J. Am. Chem. Soc. 2009, 131, 9878.
(23) Samantaray, S.; Marathe, U.; Dasgupta, S.; Nandicoori, V. K.; Roy, R. P. J. Am. Chem. Soc. 2008, 130, 2132.
(24) Popp, M. W.; Antos, J. M.; Grotenbreg, G. M.; Spooner, E.; Ploegh, H. L. Nat. Chem. Biol. 2007, 3, 707.
(25) Mao, H.; Hart, S. A.; Schink, A.; Pollok, B. A. J. Am. Chem. Soc. 2004, 126, 2670.
(26) Chen, I.; Dorr, B. M.; Liu, D. R. Proc. Natl. Acad. Sci. U.S.A. 2011, 108, 11399.
(27) Bang, D.; Pentelute, B. L.; Kent, S. B. Angew. Chem. Int. Ed. Engl. 2006, 45, 3985.
(28) Hackeng, T. M.; Griffin, J. H.; Dawson, P. E. Proc. Natl. Acad. Sci. U.S.A. 1999, 96, 10068.
(29) Young, J. A.; Collier, R. J. Annu. Rev. Biochem. 2007, 76, 243.
(30) Milne, J. C.; Blanke, S. R.; Hanna, P. C.; Collier, R. J. Mol. Microbiol. 1995, 15, 661.
(31) Collier, R. J.; Cole, H. A. Science 1969, 164, 1179.
(32) Collier, R. J. J. Mol. Biol. 1967, 25, 83.
(33) Pentelute, B. L.; Sharma, O.; Collier, R. J. Angew. Chem. Int. Ed. Engl. 2011, 50, 2294.
(34) Johnson, E. C. B.; Kent, S. B. H. J. Am. Chem. Soc. 2006, 128, 6640.
(35) Pentelute, B. L.; Sharma, O.; Collier, R. J. Angew. Chem. Int. Ed. Engl. 2011, 50, 2294.
(36) Ton-That, H.; Mazmanian, S. K.; Faull, K. F.; Schneewind, O. J. Biol. Chem. 2000, 275, 9876.
(37) Möhlmann, S.; Mahlert, C.; Greven, S.; Scholz, P.; Harrenga, A. Chembiochem 2011, 12, 1774.
(38) Johnson, E. C.; Kent, S. B. Tetrahedron. Lett. 2007, 48, 1795.
(39) Piotukh, K.; Geltinger, B.; Heinrich, N.; Gerth, F.; Beyermann, M.; Freund, C.; Schwarzer, D. J. Am. Chem. Soc. 2011, 133, 17536.
(40) Schnolzer, M.; Alewood, P.; Jones, A.; Alewood, D.; Kent, S. B. H. Int. J. Pept. Protein Res. 1992, 40, 180.
(41) Hackeng, T. M.; Griffin, J. H.; Dawson, P. E. Proc. Natl. Acad. Sci. U.S.A. 1999, 96, 10068.
(42) Kobashigawa, Y.; Kumeta, H.; Ogura, K.; Inagaki, F. J. Biomol. NMR 2009, 43, 145.

(43) Chen, I.; Dorr, B. M.; Liu, D. R. *Proc. Natl. Acad. Sci. U.S.A.* 2011, 108, 11399.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The invention claimed is:

1. A method comprising
performing a ligation reaction of a N-terminal protein domain with a peptide thioester in the presence of a cysteine transpeptidase enzyme to produce a N-terminal protein domain-COSR product,
reacting the N-terminal protein domain-COSR product with a C-terminal protein domain, wherein the C-terminal protein domain has a cysteine at the N-termini, to produce a modified protein having a chemical entity linking the N-terminal protein domain and the C-terminal protein domain.

2. The method of claim 1, wherein the cysteine transpeptidase enzyme is a SrtA enzyme.

3. The method of claim 2, wherein SrtA is SrtA*.

4. The method of claim 1, wherein the ligation reaction is performed in a sortase buffer.

5. The method of claim 1, wherein prior to the ligation reaction the N-terminal protein or N-terminal protein domain is recombinantly expressed as a SUMO-protein having a SUMO tag.

6. The method of claim 5, wherein the SUMO tag is removed using SUMO protease.

7. The method of claim 1, wherein the peptide thioester is $G_n$-Xaa-COSR (SEQ ID NOs:1-3), wherein n is 1-6 and wherein Xaa is an amino acid.

8. The method of claim 1, wherein the peptide thioester is $G_n$-Xaa-COSR (SEQ ID NOs:4-5), wherein n is 3-5 and, wherein Xaa is Gly, Phe, Ser or Leu.

9. The method of claim 1, wherein the peptide thioester is GGGGG-Xaa-COSR (SEQ ID NOs:5), wherein Xaa is Gly, Phe, Ser or Leu.

10. The method of claim 1, wherein the peptide thioester is $G_n$-$X_m$-COSR (SEQ ID NOs:6-23), wherein n is 1-6, m is 1-6, and wherein X is an amino acid, naturally occurring or non-naturally occurring.

11. The method of claim 10, wherein X is a D-amino acid (SEQ ID NOs:24-42).

12. The method of claim 1, wherein the peptide thioester is $G_n$-Y-COSR (SEQ ID NOs:43-45), wherein n is 1-6 and wherein Y is a non-amino acid chemical entity.

13. The method of claim 12, wherein in Y is a PEG unit (SEQ ID NOs:46-48).

14. The method of claim 1, wherein the method is performed without an engineered intein.

15. The method of claim 1, wherein the C-terminal protein domain and the N-terminal protein domain are protein domains of the same protein.

16. A method of producing a polypeptide library comprising
a) covalently binding a set of N-terminal protein domains to a solid support via a linker, wherein the linker comprises a cleavable moiety stable under ligating conditions and the N-terminal protein domains are each bound to the linker at its N-terminus;
b) introducing a set of peptide thioesters in the presence of a SrtA enzyme to produce a set of N-terminal protein domain-COSR products
c) introducing a set of C-terminal protein domains, having a cysteine at the N-termini, to produce a set of modified proteins having unique chemical entities linking the N-terminal protein domains and the C-terminal protein domains, wherein the set of modified proteins forms the polypeptide library.

* * * * *

```
                        SEQUENCE LISTING

<160> NUMBER OF SEQ ID NOS: 115

<210> SEQ ID NO 1
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (5)..(5)
<223> OTHER INFORMATION: Xaa is any amino acid linked to the thioester
      -COSR

<400> SEQUENCE: 1

Gly Gly Gly Gly Xaa
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(6)
<223> OTHER INFORMATION: Xaa is any amino acid linked to the thioester
      -COSR

<400> SEQUENCE: 2

Gly Gly Gly Gly Gly Xaa
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (7)..(7)
<223> OTHER INFORMATION: Xaa is any amino acid linked to the thioester
      -COSR

<400> SEQUENCE: 3

Gly Gly Gly Gly Gly Gly Xaa
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (5)..(5)
<223> OTHER INFORMATION: Xaa is Gly, Phe, Ser or Leu linked to the
      thioester -COSR

<400> SEQUENCE: 4

Gly Gly Gly Gly Xaa
```

```
<210> SEQ ID NO 5
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(6)
<223> OTHER INFORMATION: Xaa is Gly, Phe, Ser or Leu linked to the
      thioester -COSR

<400> SEQUENCE: 5

Gly Gly Gly Gly Gly Xaa
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (5)..(5)
<223> OTHER INFORMATION: Xaa is Gly, Phe, Ser or Leu linked to the
      thioester -COSR

<400> SEQUENCE: 6

Gly Gly Gly Gly Xaa
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(6)
<223> OTHER INFORMATION: Xaa is Gly, Phe, Ser or Leu linked to the
      thioester -COSR

<400> SEQUENCE: 7

Gly Gly Gly Gly Gly Xaa
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (7)..(7)
<223> OTHER INFORMATION: Xaa is Gly, Phe, Ser or Leu linked to the
      thioester -COSR

<400> SEQUENCE: 8

Gly Gly Gly Gly Gly Gly Xaa
1               5

<210> SEQ ID NO 9
<211> LENGTH: 6
<212> TYPE: PRT
<213> ORGANISM: Artificial Sequence
```

```
<220> FEATURE:
<223> OTHER INFORMATION: Synthetic Polypeptide
<220> FEATURE:
<221> NAME/KEY: MISC_FEATURE
<222> LOCATION: (5)..(6)
<223> OTHER INFORMATION: Xaa is Gly, Phe, Ser or Leu linked to the
      thioester -COSR

<400> SEQUENCE: 9

Gly Gly Gly Gly Xaa Xaa
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(7)
<223> OTHER INFORMATION: Xaa is Gly, Phe, Ser or Leu linked to the
      thioester -COSR

<400> SEQUENCE: 10

Gly Gly Gly Gly Gly Xaa Xaa
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (7)..(8)
<223> OTHER INFORMATION: Xaa is Gly, Phe, Ser or Leu linked to the
      thioester -COSR

<400> SEQUENCE: 11

Gly Gly Gly Gly Gly Gly Xaa Xaa
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (5)..(7)
<223> OTHER INFORMATION: Xaa is Gly, Phe, Ser or Leu linked to the
      thioester -COSR

<400> SEQUENCE: 12

Gly Gly Gly Gly Xaa Xaa Xaa
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(8)
<223> OTHER INFORMATION: Xaa is Gly, Phe, Ser or Leu linked to the
      thioester -COSR
```

<400> SEQUENCE: 13

Gly Gly Gly Gly Gly Xaa Xaa Xaa
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (7)..(9)
<223> OTHER INFORMATION: Xaa is Gly, Phe, Ser or Leu linked to the
      thioester -COSR

<400> SEQUENCE: 14

Gly Gly Gly Gly Gly Gly Xaa Xaa Xaa
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (5)..(8)
<223> OTHER INFORMATION: Xaa is Gly, Phe, Ser or Leu linked to the
      thioester -COSR

<400> SEQUENCE: 15

Gly Gly Gly Gly Xaa Xaa Xaa Xaa
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(9)
<223> OTHER INFORMATION: Xaa is Gly, Phe, Ser or Leu linked to the
      thioester -COSR

<400> SEQUENCE: 16

Gly Gly Gly Gly Gly Xaa Xaa Xaa Xaa
1               5

<210> SEQ ID NO 17
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (7)..(10)
<223> OTHER INFORMATION: Xaa is Gly, Phe, Ser or Leu linked to the
      thioester -COSR

<400> SEQUENCE: 17

Gly Gly Gly Gly Gly Gly Xaa Xaa Xaa Xaa
1               5                   10

```
<210> SEQ ID NO 18
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (5)..(9)
<223> OTHER INFORMATION: Xaa is Gly, Phe, Ser or Leu linked to the
      thioester -COSR

<400> SEQUENCE: 18

Gly Gly Gly Gly Xaa Xaa Xaa Xaa Xaa
1               5

<210> SEQ ID NO 19
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(10)
<223> OTHER INFORMATION: Xaa is Gly, Phe, Ser or Leu linked to the
      thioester -COSR

<400> SEQUENCE: 19

Gly Gly Gly Gly Gly Xaa Xaa Xaa Xaa Xaa
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (7)..(11)
<223> OTHER INFORMATION: Xaa is Gly, Phe, Ser or Leu linked to the
      thioester -COSR

<400> SEQUENCE: 20

Gly Gly Gly Gly Gly Gly Xaa Xaa Xaa Xaa Xaa
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (5)..(10)
<223> OTHER INFORMATION: Xaa is Gly, Phe, Ser or Leu linked to the
      thioester -COSR

<400> SEQUENCE: 21

Gly Gly Gly Gly Xaa Xaa Xaa Xaa Xaa Xaa
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
```

```
<221> NAME/KEY: MISC_FEATURE
<222> LOCATION: (6)..(11)
<223> OTHER INFORMATION: Xaa is Gly, Phe, Ser or Leu linked to the
      thioester -COSR

<400> SEQUENCE: 22

Gly Gly Gly Gly Gly Xaa Xaa Xaa Xaa Xaa Xaa
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (7)..(12)
<223> OTHER INFORMATION: Xaa is Gly, Phe, Ser or Leu linked to the
      thioester -COSR

<400> SEQUENCE: 23

Gly Gly Gly Gly Gly Gly Xaa Xaa Xaa Xaa Xaa Xaa
1               5                   10

<210> SEQ ID NO 24
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (5)..(5)
<223> OTHER INFORMATION: Xaa is a D-amino acid linked to the thioester
      -COSR

<400> SEQUENCE: 24

Gly Gly Gly Gly Xaa
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(6)
<223> OTHER INFORMATION: Xaa is a D-amino acid linked to the thioester
      -COSR

<400> SEQUENCE: 25

Gly Gly Gly Gly Gly Xaa
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (7)..(7)
<223> OTHER INFORMATION: Xaa is a D-amino acid linked to the thioester
      -COSR

<400> SEQUENCE: 26
```

```
Gly Gly Gly Gly Gly Gly Xaa
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (5)..(6)
<223> OTHER INFORMATION: Xaa is a D-amino acid linked to the thioester
      -COSR

<400> SEQUENCE: 27

Gly Gly Gly Gly Xaa Xaa
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(7)
<223> OTHER INFORMATION: Xaa is a D-amino acid linked to the thioester
      COSR

<400> SEQUENCE: 28

Gly Gly Gly Gly Gly Xaa Xaa
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (7)..(8)
<223> OTHER INFORMATION: Xaa is a D-amino acid linked to the thioester
      -COSR

<400> SEQUENCE: 29

Gly Gly Gly Gly Gly Gly Xaa Xaa
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (5)..(7)
<223> OTHER INFORMATION: Xaa is a D-amino acid linked to the thioester
      -COSR

<400> SEQUENCE: 30

Gly Gly Gly Gly Xaa Xaa Xaa
1               5

<210> SEQ ID NO 31
<211> LENGTH: 8
<212> TYPE: PRT
```

```
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(8)
<223> OTHER INFORMATION: Xaa is a D-amino acid linked to the thioester
      -COSR

<400> SEQUENCE: 31

Gly Gly Gly Gly Gly Xaa Xaa Xaa
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (7)..(9)
<223> OTHER INFORMATION: Xaa is a D-amino acid linked to the thioester
      -COSR

<400> SEQUENCE: 32

Gly Gly Gly Gly Gly Gly Xaa Xaa Xaa
1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (5)..(8)
<223> OTHER INFORMATION: Xaa is a D-amino acid linked to the thioester
      -COSR

<400> SEQUENCE: 33

Gly Gly Gly Gly Xaa Xaa Xaa Xaa
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(9)
<223> OTHER INFORMATION: Xaa is a D-amino acid linked to the thioester
      -COSR

<400> SEQUENCE: 34

Gly Gly Gly Gly Gly Xaa Xaa Xaa Xaa
1               5

<210> SEQ ID NO 35
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (7)..(10)
<223> OTHER INFORMATION: Xaa is a D-amino acid linked to the thioester
```

-COSR

<400> SEQUENCE: 35

Gly Gly Gly Gly Gly Gly Xaa Xaa Xaa Xaa
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (7)..(10)
<223> OTHER INFORMATION: Xaa is a D-amino acid linked to the thioester
      -COSR

<400> SEQUENCE: 36

Gly Gly Gly Gly Gly Gly Xaa Xaa Xaa Xaa
1               5                   10

<210> SEQ ID NO 37
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (5)..(9)
<223> OTHER INFORMATION: Xaa is a D-amino acid linked to the thioester
      -COSR

<400> SEQUENCE: 37

Gly Gly Gly Gly Xaa Xaa Xaa Xaa Xaa
1               5

<210> SEQ ID NO 38
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(10)
<223> OTHER INFORMATION: Xaa is a D-amino acid linked to the thioester
      -COSR

<400> SEQUENCE: 38

Gly Gly Gly Gly Gly Xaa Xaa Xaa Xaa Xaa
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (7)..(11)
<223> OTHER INFORMATION: Xaa is a D-amino acid linked to the thioester
      -COSR

<400> SEQUENCE: 39

Gly Gly Gly Gly Gly Gly Xaa Xaa Xaa Xaa Xaa
1               5                   10

```
<210> SEQ ID NO 40
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (5)..(10)
<223> OTHER INFORMATION: Xaa is a D-amino acid linked to the thioester
      -COSR

<400> SEQUENCE: 40

Gly Gly Gly Gly Xaa Xaa Xaa Xaa Xaa Xaa
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(11)
<223> OTHER INFORMATION: Xaa is a D-amino acid linked to the thioester
      -COSR

<400> SEQUENCE: 41

Gly Gly Gly Gly Gly Xaa Xaa Xaa Xaa Xaa Xaa
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (7)..(12)
<223> OTHER INFORMATION: Xaa is a D-amino acid linked to the thioester
      -COSR

<400> SEQUENCE: 42

Gly Gly Gly Gly Gly Gly Xaa Xaa Xaa Xaa Xaa Xaa
1               5                   10

<210> SEQ ID NO 43
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (4)..(4)
<223> OTHER INFORMATION: Xaa is Gly linked to Y, a non-amino acid
      chemical entity which is linked to -COSR, a thioester

<400> SEQUENCE: 43

Gly Gly Gly Xaa
1

<210> SEQ ID NO 44
<211> LENGTH: 5
<212> TYPE: PRT
<213> ORGANISM: Artificial Sequence
<220> FEATURE:
<223> OTHER INFORMATION: Synthetic Polypeptide
```

```
<220> FEATURE:
<221> NAME/KEY: MISC_FEATURE
<222> LOCATION: (5)..(5)
<223> OTHER INFORMATION: Xaa is Gly linked to Y, a non-amino acid
      chemical entity which is linked to -COSR, a thioester

<400> SEQUENCE: 44

Gly Gly Gly Gly Xaa
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(6)
<223> OTHER INFORMATION: Xaa is Gly linked to Y, a non-amino acid
      chemical entity which is linked to -COSR, a thioester

<400> SEQUENCE: 45

Gly Gly Gly Gly Gly Xaa
1               5

<210> SEQ ID NO 46
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (4)..(4)
<223> OTHER INFORMATION: Xaa is Gly linked to Y(a PEG unit)-
      COSR(thioester)

<400> SEQUENCE: 46

Gly Gly Gly Xaa
1

<210> SEQ ID NO 47
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (5)..(5)
<223> OTHER INFORMATION: Xaa is Gly linked to Y(a PEG unit)-
      COSR(thioester)

<400> SEQUENCE: 47

Gly Gly Gly Gly Xaa
1               5

<210> SEQ ID NO 48
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(6)
<223> OTHER INFORMATION: Xaa is Gly linked to Y(a PEG unit)-
      COSR(thioester)

<400> SEQUENCE: 48
```

Gly Gly Gly Gly Gly Xaa
1               5

<210> SEQ ID NO 49
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(6)
<223> OTHER INFORMATION: Xaa is Phe attached to the thioester COSR

<400> SEQUENCE: 49

Gly Gly Gly Gly Gly Xaa
1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 50

Lys Leu Pro Glu Thr Gly Gly
1               5

<210> SEQ ID NO 51
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is Leu attached to a protein

<400> SEQUENCE: 51

Xaa Pro Ser Thr Gly Gly
1               5

<210> SEQ ID NO 52
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is His6-SUMO-LFN- attached to Leu

<400> SEQUENCE: 52

Xaa Pro Ser Thr Gly Gly His His His His His His
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is His6-SUMO-LFN-DTA- attached to Leu

<400> SEQUENCE: 53

Xaa Pro Ser Thr Gly Gly His His His His His
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is His6-SUMO-LFN-DTA-EGFP- attached to L

<400> SEQUENCE: 54

Xaa Pro Ser Thr Gly Gly His His His His His
1               5                   10

<210> SEQ ID NO 55
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is LFN- attached to Gly
<220> FEATURE:
<221> NAME/KEY: MISC_FEATURE
<222> LOCATION: (6)..(6)
<223> OTHER INFORMATION: Xaa is Phe attached to thioester -COSR

<400> SEQUENCE: 55

Xaa Gly Gly Gly Gly Xaa
1               5

<210> SEQ ID NO 56
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is LFN-DTA- attached to Gly
<220> FEATURE:
<221> NAME/KEY: MISC_FEATURE
<222> LOCATION: (6)..(6)
<223> OTHER INFORMATION: Xaa is Phe attached to thioester -COSR

<400> SEQUENCE: 56

Xaa Gly Gly Gly Gly Xaa
1               5

<210> SEQ ID NO 57
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is eGFP- attached to Gly
<220> FEATURE:
<221> NAME/KEY: MISC_FEATURE
<222> LOCATION: (6)..(6)

```
<223> OTHER INFORMATION: Xaa is Phe attached to thioester -COSR

<400> SEQUENCE: 57

Xaa Gly Gly Gly Gly Xaa
1               5

<210> SEQ ID NO 58
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is EGFP attached to Cys

<400> SEQUENCE: 58

Xaa Phe Arg Ala Leu Lys Ala Ala
1               5

<210> SEQ ID NO 59
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 59

Ala Phe Leu Pro Ser Thr Gly Gly
1               5

<210> SEQ ID NO 60
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (5)..(5)
<223> OTHER INFORMATION: Xaa is Gly attached to thioester COSR

<400> SEQUENCE: 60

Gly Gly Gly Gly Xaa
1               5

<210> SEQ ID NO 61
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (3)..(3)
<223> OTHER INFORMATION: Any amino acid

<400> SEQUENCE: 61

Leu Pro Xaa Thr Gly
1               5

<210> SEQ ID NO 62
<211> LENGTH: 6
<212> TYPE: PRT
<213> ORGANISM: Artificial Sequence
<220> FEATURE:
<223> OTHER INFORMATION: Synthetic Polypeptide
```

```
<400> SEQUENCE: 62

Leu Pro Ser Thr Gly Gly
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (3)..(3)
<223> OTHER INFORMATION: Any amino acid

<400> SEQUENCE: 63

Leu Pro Xaa Thr Gly Gly Gly Gly Gly
1               5

<210> SEQ ID NO 64
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (3)..(3)
<223> OTHER INFORMATION: Any amino acid

<400> SEQUENCE: 64

Phe Pro Xaa Thr Gly
1               5

<210> SEQ ID NO 65
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (3)..(3)
<223> OTHER INFORMATION: Any amino acid

<400> SEQUENCE: 65

Ala Pro Xaa Thr Gly
1               5

<210> SEQ ID NO 66
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(6)
<223> OTHER INFORMATION: Xaa is Gly attached to -MPA-LR-CONH2

<400> SEQUENCE: 66

Gly Gly Gly Gly Gly Xaa
1               5

<210> SEQ ID NO 67
<211> LENGTH: 6
<212> TYPE: PRT
<213> ORGANISM: Artificial Sequence
<220> FEATURE:
```

<223> OTHER INFORMATION: Synthetic Polypeptide
<220> FEATURE:
<221> NAME/KEY: MISC_FEATURE
<222> LOCATION: (6)..(6)
<223> OTHER INFORMATION: Xaa is Phe attached to -MPA-LR-CONH2

<400> SEQUENCE: 67

Gly Gly Gly Gly Gly Xaa
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(6)
<223> OTHER INFORMATION: Xaa is Ser attached to -MPA-LR-CONH2

<400> SEQUENCE: 68

Gly Gly Gly Gly Gly Xaa
1               5

<210> SEQ ID NO 69
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(6)
<223> OTHER INFORMATION: Xaa is Leu attached to -MPA-LR-CONH2

<400> SEQUENCE: 69

Gly Gly Gly Gly Gly Xaa
1               5

<210> SEQ ID NO 70
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (5)..(5)
<223> OTHER INFORMATION: Xaa is Gly attached to -MPA-LR-CONH2

<400> SEQUENCE: 70

Gly Gly Gly Gly Xaa
1               5

<210> SEQ ID NO 71
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (4)..(4)
<223> OTHER INFORMATION: Xaa is Gly attached to -MPA-LR-CONH2

<400> SEQUENCE: 71

Gly Gly Gly Xaa
1

```
<210> SEQ ID NO 72
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (13)..(13)
<223> OTHER INFORMATION: Xaa is Gly attached to -MPA-LL-CONH2

<400> SEQUENCE: 72

Gly Gly Gly Gly Gly Ser Gly Arg Glu Leu Glu Arg Xaa
1               5                   10

<210> SEQ ID NO 73
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (13)..(13)
<223> OTHER INFORMATION: Xaa is Gly attached to -MPA-LL-CONH2

<400> SEQUENCE: 73

Gly Gly Gly Gly Gly Ser Gly Arg Glu Leu Glu Arg Xaa
1               5                   10

<210> SEQ ID NO 74
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (7)..(7)
<223> OTHER INFORMATION: Xaa is Gly attached to CONH2

<400> SEQUENCE: 74

Lys Leu Pro Glu Thr Gly Xaa
1               5

<210> SEQ ID NO 75
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 75

Cys Phe Arg Ala Leu Lys Ala Ala
1               5

<210> SEQ ID NO 76
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 76

Gly Gly Gly Gly Gly Leu Arg Leu
1               5

<210> SEQ ID NO 77
```

```
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (11)..(11)
<223> OTHER INFORMATION: Xaa is Phe attached to thioester -COSR

<400> SEQUENCE: 77

Lys Leu Pro Glu Thr Gly Gly Gly Gly Gly Xaa
1               5                   10

<210> SEQ ID NO 78
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is eGFP- attached to Leu
<220> FEATURE:
<221> NAME/KEY: MISC_FEATURE
<222> LOCATION: (10)..(0)
<223> OTHER INFORMATION: Xaa is Phe attached to thioester -COSR
<220> FEATURE:
<221> NAME/KEY: misc_feature
<222> LOCATION: (10)..(10)
<223> OTHER INFORMATION: Xaa can be any naturally occurring amino acid

<400> SEQUENCE: 78

Xaa Pro Ser Thr Gly Gly Gly Gly Gly Xaa
1               5                   10

<210> SEQ ID NO 79
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 79

Lys Leu Pro Glu Thr Gly Gly Gly Gly Gly Phe Cys Phe Arg Ala Leu
1               5                   10                  15

Lys Ala Ala

<210> SEQ ID NO 80
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is His6-SUMO-eGFP- attached to Leu

<400> SEQUENCE: 80

Xaa Pro Ser Thr Gly Gly His His His His His His
1               5                   10

<210> SEQ ID NO 81
<211> LENGTH: 49
<212> TYPE: DNA
<213> ORGANISM: Artificial Sequence
<220> FEATURE:
<223> OTHER INFORMATION: Synthetic Polynucleotide
```

```
<400> SEQUENCE: 81
atggtgagca agggcgagga gctgttcacc ggggtggtgc ccatcctgg            49

<210> SEQ ID NO 82
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 82
ctaatggtgg tggtggtggt ggccgccggt gctcggcagc ttgtacagct cgtccatgc   59

<210> SEQ ID NO 83
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 83
gaaggagata tacatatgat cagcagccat catcatcatc                      40

<210> SEQ ID NO 84
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 84
ccaggaccag caacatccga acaattaaat agaggtg                         37

<210> SEQ ID NO 85
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 85
gtataaaatg acaagtataa gaaacgttaa gccaacagat gtagaag              47

<210> SEQ ID NO 86
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 86
gacaggcgtt tgggaaaccc gtaaaatctt tgtag                           35

<210> SEQ ID NO 87
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is His6-SUMO-LFN- attached to Leu

<400> SEQUENCE: 87
```

Xaa Pro Ser Thr Gly Gly His His His His His His
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is His6-SUMO-LFN-DTA(C186S)- attached to
      Leu

<400> SEQUENCE: 88

Xaa Pro Ser Thr Gly Gly His His His His His His
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12)..(12)
<223> OTHER INFORMATION: Xaa is Arg attached to thioester -COSR

<400> SEQUENCE: 89

Gly Gly Gly Gly Gly Ser Gly Arg Glu Leu Glu Xaa
1               5                   10

<210> SEQ ID NO 90
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is a protein attached to Leu
<220> FEATURE:
<221> NAME/KEY: MISC_FEATURE
<222> LOCATION: (9)..(9)
<223> OTHER INFORMATION: Xaa is Gly attached to -linker-COSR(thioester)

<400> SEQUENCE: 90

Xaa Pro Ser Thr Gly Gly Gly Gly Xaa
1               5

<210> SEQ ID NO 91
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (5)..(5)
<223> OTHER INFORMATION: Xaa is Gly attached to an L-linker-
      COSR(thioester)

<400> SEQUENCE: 91

Gly Gly Gly Gly Xaa
1               5

<210> SEQ ID NO 92

```
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (5)..(5)
<223> OTHER INFORMATION: Xaa is Gly attached to a D-linker-
      COSR(thioester)

<400> SEQUENCE: 92

Gly Gly Gly Gly Xaa
1               5

<210> SEQ ID NO 93
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is LFN attached to Ser
<220> FEATURE:
<221> NAME/KEY: MISC_FEATURE
<222> LOCATION: (7)..(7)
<223> OTHER INFORMATION: Xaa is Arg attached to thioester -COSR

<400> SEQUENCE: 93

Xaa Gly Arg Glu Leu Glu Xaa
1               5

<210> SEQ ID NO 94
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is eGFP- attached to Leu

<400> SEQUENCE: 94

Xaa Pro Ser Thr Gly Gly His His His His His His
1               5                   10

<210> SEQ ID NO 95
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 95

Gly Gly Gly Gly Gly Leu Arg Leu
1               5

<210> SEQ ID NO 96
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is LFN-DTA- attached to Leu
<220> FEATURE:
```

```
<221> NAME/KEY: MISC_FEATURE
<222> LOCATION: (10)..(10)
<223> OTHER INFORMATION: Xaa is Phe attached to thioester COSR

<400> SEQUENCE: 96

Xaa Pro Ser Thr Gly Gly Gly Gly Gly Xaa
1               5                   10

<210> SEQ ID NO 97
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (7)..(7)
<223> OTHER INFORMATION: Xaa is Gly attached to -COSR

<400> SEQUENCE: 97

Lys Leu Pro Glu Thr Gly Xaa
1               5

<210> SEQ ID NO 98
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(6)
<223> OTHER INFORMATION: Xaa is Gly attached to thioester COSR

<400> SEQUENCE: 98

Lys Leu Pro Glu Thr Xaa
1               5

<210> SEQ ID NO 99
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (8)..(8)
<223> OTHER INFORMATION: Xaa is Ala attached to thioester -COSR
<220> FEATURE:
<221> NAME/KEY: misc_feature
<222> LOCATION: (9)..(9)
<223> OTHER INFORMATION: Xaa can be any naturally occurring amino acid

<400> SEQUENCE: 99

Gly Gly Gly Gly Gly Asn Asn Ala Xaa
1               5

<210> SEQ ID NO 100
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 100

Asn Asn Ala Ala
1

<210> SEQ ID NO 101
```

```
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is SUMO- attached to Ala

<400> SEQUENCE: 101

Xaa Phe Leu Pro Ser Thr Gly Gly
1               5

<210> SEQ ID NO 102
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 102

Ala Phe Leu Pro Ser Thr Gly Gly
1               5

<210> SEQ ID NO 103
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (11)..(11)
<223> OTHER INFORMATION: Xaa is Gly attached to thioester -COSR

<400> SEQUENCE: 103

Ala Phe Leu Pro Ser Thr Gly Gly Gly Gly Xaa
1               5                   10

<210> SEQ ID NO 104
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 104

Gly Gly Gly Gly Gly
1               5

<210> SEQ ID NO 105
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 105

Ala Phe Gly Gly Gly Gly Gly Gly
1               5

<210> SEQ ID NO 106
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
```

```
<221> NAME/KEY: MISC_FEATURE
<222> LOCATION: (5)..(5)
<223> OTHER INFORMATION: Xaa is Gly attached to 10FN3

<400> SEQUENCE: 106

Gly Gly Gly Gly Xaa
1               5

<210> SEQ ID NO 107
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (4)..(4)
<223> OTHER INFORMATION: Xaa is Gly attached to -LRL-CONH2

<400> SEQUENCE: 107

Gly Gly Gly Xaa
1

<210> SEQ ID NO 108
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is eGFP attached to Leu
<220> FEATURE:
<221> NAME/KEY: MISC_FEATURE
<222> LOCATION: (1)..(1)
<223> OTHER INFORMATION: Xaa is eGFP- attached to Leu

<400> SEQUENCE: 108

Xaa Pro Ser Thr Gly Gly Gly Gly Gly Leu Arg Leu
1               5                   10

<210> SEQ ID NO 109
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is LFN- attached to Leu

<400> SEQUENCE: 109

Xaa Pro Ser Thr Gly Gly His His His His His His
1               5                   10

<210> SEQ ID NO 110
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (5)..(5)
<223> OTHER INFORMATION: Xaa is Gly attached to an affibody

<400> SEQUENCE: 110

Gly Gly Gly Gly Xaa
```

```
1               5

<210> SEQ ID NO 111
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is LFN- attached to Leu
<220> FEATURE:
<221> NAME/KEY: MISC_FEATURE
<222> LOCATION: (9)..(9)
<223> OTHER INFORMATION: Xaa is Gly attached to an affibody

<400> SEQUENCE: 111

Xaa Pro Ser Thr Gly Gly Gly Gly Xaa
1               5

<210> SEQ ID NO 112
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (5)..(5)
<223> OTHER INFORMATION: Xaa is Gly attached to 2Dpico

<400> SEQUENCE: 112

Gly Gly Gly Gly Xaa
1               5

<210> SEQ ID NO 113
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is LFN attached to Leu
<220> FEATURE:
<221> NAME/KEY: MISC_FEATURE
<222> LOCATION: (9)..(9)
<223> OTHER INFORMATION: Xaa is Gly attached to -10FN3

<400> SEQUENCE: 113

Xaa Pro Ser Thr Gly Gly Gly Gly Xaa
1               5

<210> SEQ ID NO 114
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is LFN attached to Leu
<220> FEATURE:
<221> NAME/KEY: MISC_FEATURE
<222> LOCATION: (9)..(9)
<223> OTHER INFORMATION: Xaa is Gly attached to 2Dpic

<400> SEQUENCE: 114
```

```
Xaa Pro Ser Thr Gly Gly Gly Gly Xaa
1               5
```

```
<210> SEQ ID NO 115
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 115

Ala Phe Leu Pro Ser Thr Gly Gly
1               5
```